US009877776B2

(12) United States Patent
Boudreaux

(10) Patent No.: US 9,877,776 B2
(45) Date of Patent: Jan. 30, 2018

(54) SIMULTANEOUS I-BEAM AND SPRING DRIVEN CAM JAW CLOSURE MECHANISM

(71) Applicant: Ethicon Endo-Surgery, Inc., Cincinnati, OH (US)

(72) Inventor: Chad P. Boudreaux, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 462 days.

(21) Appl. No.: 14/467,883

(22) Filed: Aug. 25, 2014

(65) Prior Publication Data

US 2016/0051315 A1 Feb. 25, 2016

(51) Int. Cl.
*A61B 18/14* (2006.01)
*A61B 18/00* (2006.01)

(52) U.S. Cl.
CPC ........ *A61B 18/1445* (2013.01); *A61B 18/148* (2013.01); *A61B 18/1447* (2013.01); *A61B 18/1482* (2013.01); *A61B 18/1485* (2013.01); *A61B 2018/0063* (2013.01); *A61B 2018/0094* (2013.01); *A61B 2018/00196* (2013.01);
(Continued)

(58) Field of Classification Search
CPC ............ A61B 18/1445; A61B 18/1452; A61B 18/1447; A61B 18/1455; A61B 18/1482; A61B 2018/00196; A61B 2017/2922; A61B 18/148; A61B 18/1485; A61B 2018/00595; A61B 2018/00601;
(Continued)

(56) References Cited

U.S. PATENT DOCUMENTS 2,366,274 A 1/1945 Luth et al.
2,458,152 A 1/1949 Eakins
(Continued)

FOREIGN PATENT DOCUMENTS

CN 2868227 Y 2/2007
DE 4300307 A1 7/1994
(Continued)

OTHER PUBLICATIONS

International Search Report, Application No. PCT/US2015/044210, dated Feb. 24, 2016 (6 pages).
(Continued)

*Primary Examiner* — Ronald Hupczey, Jr.
*Assistant Examiner* — Tigist Demie

(57) ABSTRACT

A surgical instrument includes an end effector and a handle assembly. The end effector includes a movable jaw and a cutting element slidably movable within the end effector. The handle assembly includes an energy button configured to deliver energy to at least one electrode located in the end effector, a trigger plate operably coupled to a jaw closure mechanism, the trigger plate configured to close the movable jaw, a firing plate operably coupled to a cutting element drive mechanism. The firing plate is configured to drive the cutting element independently of the jaw closure mechanism. The cutting element drive mechanism is configured to close the movable jaw when the cutting element is driven. The handle assembly further includes a trigger operatively coupled to the trigger plate and the firing plate. The jaw closure mechanism and the cutting element drive mechanism are configured to simultaneously close the movable jaw.

20 Claims, 26 Drawing Sheets

(52) U.S. Cl.
CPC .............. *A61B 2018/00595* (2013.01); *A61B 2018/00601* (2013.01); *A61B 2018/00922* (2013.01); *A61B 2018/00946* (2013.01); *A61B 2018/00958* (2013.01); *A61B 2018/1455* (2013.01)

(58) Field of Classification Search
CPC .. A61B 2018/0063; A61B 2018/00922; A61B 2018/0094; A61B 2018/00946
See application file for complete search history.

(56) References Cited

U.S. PATENT DOCUMENTS

| | | |
|---|---|---|
| 2,510,693 A | 6/1950 | Green |
| 2,867,039 A | 1/1959 | Zach |
| 3,166,971 A | 1/1965 | Stoecker |
| 3,525,912 A | 8/1970 | Wallin |
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,203,430 A | 5/1980 | Takahashi |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,880,015 A | 11/1989 | Nierman |
| 4,910,389 A | 3/1990 | Sherman et al. |
| 4,920,978 A | 5/1990 | Colvin |
| 4,936,842 A | 6/1990 | D'Amelio et al. |
| 5,020,514 A | 6/1991 | Heckele |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,312,023 A | 5/1994 | Green et al. |
| 5,318,563 A | 6/1994 | Malis et al. |
| 5,318,564 A | 6/1994 | Eggers |
| 5,318,589 A | 6/1994 | Lichtman |
| 5,326,013 A | 7/1994 | Green et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,456,684 A | 10/1995 | Schmidt et al. |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,681 A | 7/1996 | Strul et al. |
| 5,542,916 A | 8/1996 | Hirsch et al. |
| 5,558,671 A | 9/1996 | Yates |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,607,450 A | 3/1997 | Zvenyatsky et al. |
| 5,611,813 A | 3/1997 | Lichtman |
| 5,618,307 A | 4/1997 | Donlon et al. |
| 5,624,452 A | 4/1997 | Yates |
| 5,632,432 A | 5/1997 | Schulze et al. |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman |
| 5,836,909 A | 11/1998 | Cosmescu |
| 5,836,943 A | 11/1998 | Miller, III |

(56) References Cited

U.S. PATENT DOCUMENTS

| | | |
|---|---|---|
| 5,836,990 A | 11/1998 | Li |
| 5,853,412 A | 12/1998 | Mayenberger |
| 5,876,401 A | 3/1999 | Schulze et al. |
| 5,878,193 A | 3/1999 | Wang et al. |
| 5,880,668 A | 3/1999 | Hall |
| 5,891,142 A | 4/1999 | Eggers et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| H1904 H | 10/2000 | Yates et al. |
| 6,132,368 A | 10/2000 | Cooper |
| 6,144,402 A | 11/2000 | Norsworthy et al. |
| 6,152,923 A | 11/2000 | Ryan |
| 6,154,198 A | 11/2000 | Rosenberg |
| 6,162,208 A | 12/2000 | Hipps |
| 6,174,309 B1 | 1/2001 | Wrublewski et al. |
| 6,176,857 B1 | 1/2001 | Ashley |
| 6,190,386 B1 | 2/2001 | Rydell |
| 6,206,876 B1 | 3/2001 | Levine et al. |
| 6,228,080 B1 | 5/2001 | Gines |
| 6,231,565 B1 | 5/2001 | Tovey et al. |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,364,888 B1 | 4/2002 | Niemeyer et al. |
| 6,387,109 B1 | 5/2002 | Davison et al. |
| 6,391,026 B1 | 5/2002 | Hung et al. |
| 6,398,779 B1 | 6/2002 | Buysse et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,689 B1 | 10/2002 | Qin et al. |
| 6,464,702 B2 | 10/2002 | Schulze et al. |
| 6,480,796 B2 | 11/2002 | Wiener |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,551,309 B1 | 4/2003 | LePivert |
| 6,554,829 B2 | 4/2003 | Schulze et al. |
| 6,558,376 B2 | 5/2003 | Bishop |
| 6,562,037 B2 | 5/2003 | Paton et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,644,532 B2 | 11/2003 | Green et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,673,248 B2 | 1/2004 | Chowdhury |
| 6,679,882 B1 | 1/2004 | Kornerup |
| 6,695,840 B2 | 2/2004 | Schulze |
| 6,722,552 B2 | 4/2004 | Fenton, Jr. |
| 6,746,443 B1 | 6/2004 | Morley et al. |
| 6,752,815 B2 | 6/2004 | Beaupre |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,783,524 B2 | 8/2004 | Anderson et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,877,647 B2 | 4/2005 | Green et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 6,977,495 B2 | 12/2005 | Donofrio |
| 6,994,709 B2 | 2/2006 | Iida |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,077,853 B2 | 7/2006 | Kramer et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |

(56) References Cited

U.S. PATENT DOCUMENTS

| | | |
|---|---|---|
| 7,252,667 B2 | 8/2007 | Moses et al. |
| 7,267,677 B2 | 9/2007 | Johnson et al. |
| 7,267,685 B2 | 9/2007 | Butaric et al. |
| 7,273,483 B2 | 9/2007 | Wiener et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,416,101 B2 | 8/2008 | Shelton, IV et al. |
| 7,422,139 B2 | 9/2008 | Shelton, IV et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,543,730 B1 | 6/2009 | Marczyk |
| 7,550,216 B2 | 6/2009 | Ofer et al. |
| 7,553,309 B2 | 6/2009 | Buysse et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,751 B2 | 5/2010 | Hughes et al. |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,726,537 B2 | 6/2010 | Olson et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,210 B2 | 8/2010 | Shelton, IV et al. |
| 7,766,910 B2 | 8/2010 | Hixson et al. |
| 7,770,775 B2 | 8/2010 | Shelton, IV et al. |
| 7,775,972 B2 | 8/2010 | Brock et al. |
| 7,776,037 B2 | 8/2010 | Odom |
| 7,780,651 B2 | 8/2010 | Madhani et al. |
| 7,780,663 B2 | 8/2010 | Yates et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,861,906 B2 | 1/2011 | Doll et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| 7,935,114 B2 | 5/2011 | Takashino et al. |
| 7,951,165 B2 | 5/2011 | Golden et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,038,693 B2 | 10/2011 | Allen |
| 8,056,720 B2 | 11/2011 | Hawkes |
| 8,058,771 B2 | 11/2011 | Giordano et al. |
| 8,061,014 B2 | 11/2011 | Smith et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,221,415 B2 | 7/2012 | Francischelli |
| 8,236,020 B2 | 8/2012 | Smith et al. |
| 8,241,235 B2 | 8/2012 | Kahler et al. |
| 8,241,284 B2 | 8/2012 | Dycus et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,333,778 B2 | 12/2012 | Smith et al. |
| 8,333,779 B2 | 12/2012 | Smith et al. |
| 8,334,468 B2 | 12/2012 | Palmer et al. |
| 8,338,726 B2 | 12/2012 | Palmer et al. |
| 8,357,158 B2 | 1/2013 | McKenna et al. |
| 8,372,099 B2 | 2/2013 | Deville et al. |

(56) References Cited

U.S. PATENT DOCUMENTS

| | | |
|---|---|---|
| 8,372,101 B2 | 2/2013 | Smith et al. |
| 8,377,059 B2 | 2/2013 | Deville et al. |
| 8,377,085 B2 | 2/2013 | Smith et al. |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,430,876 B2 | 4/2013 | Kappus et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,496,682 B2 | 7/2013 | Guerra et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| D695,407 S | 12/2013 | Price et al. |
| 8,613,383 B2 | 12/2013 | Beckman et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,647,350 B2 | 2/2014 | Mohan et al. |
| 8,663,220 B2 | 3/2014 | Wiener et al. |
| 8,663,222 B2 | 3/2014 | Anderson et al. |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,028,494 B2 | 5/2015 | Shelton, IV et al. |
| 9,028,519 B2 | 5/2015 | Yates et al. |
| 9,044,243 B2 | 6/2015 | Johnson et al. |
| 9,044,256 B2 | 6/2015 | Cadeddu et al. |
| 9,055,961 B2 | 6/2015 | Manzo et al. |
| 9,060,770 B2 | 6/2015 | Shelton, IV et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,101,385 B2 | 8/2015 | Shelton, IV et al. |
| 9,119,657 B2 | 9/2015 | Shelton, IV et al. |
| 9,125,662 B2 | 9/2015 | Shelton, IV |
| 9,149,324 B2 | 10/2015 | Huang et al. |
| 9,149,325 B2 | 10/2015 | Worrell et al. |
| 9,168,085 B2 | 10/2015 | Juzkiw et al. |
| 9,179,912 B2 | 11/2015 | Yates et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,259,265 B2 | 2/2016 | Harris et al. |
| 9,265,926 B2 | 2/2016 | Strobl et al. |
| 9,277,962 B2 | 3/2016 | Koss et al. |
| 9,283,027 B2 | 3/2016 | Monson et al. |
| 9,283,045 B2 | 3/2016 | Rhee et al. |
| 9,295,514 B2 | 3/2016 | Shelton, IV et al. |
| 9,314,292 B2 | 4/2016 | Trees et al. |
| 9,326,788 B2 | 5/2016 | Batross et al. |
| 9,333,025 B2 | 5/2016 | Monson et al. |
| 9,351,754 B2 | 5/2016 | Vakharia et al. |
| 9,375,232 B2 | 6/2016 | Hunt et al. |
| 9,375,267 B2 | 6/2016 | Kerr et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 2002/0022836 A1 | 2/2002 | Goble et al. |
| 2002/0049551 A1 | 4/2002 | Friedman et al. |
| 2002/0107517 A1 | 8/2002 | Witt et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0054364 A1 | 3/2004 | Aranyi et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193148 A1 | 9/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |

(56) References Cited

U.S. PATENT DOCUMENTS

| | | |
|---|---|---|
| 2005/0103819 A1 | 5/2005 | Racenet et al. |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0256405 A1 | 11/2005 | Makin et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0058825 A1 | 3/2006 | Ogura et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0182322 A1 | 8/2006 | Bernhardt et al. |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0106317 A1 | 5/2007 | Shelton, IV et al. |
| 2007/0118115 A1 | 5/2007 | Artale et al. |
| 2007/0146113 A1 | 6/2007 | Truckai et al. |
| 2007/0173803 A1 | 7/2007 | Wham et al. |
| 2007/0173811 A1 | 7/2007 | Couture et al. |
| 2007/0173813 A1 | 7/2007 | Odom |
| 2007/0175949 A1 | 8/2007 | Shelton, IV et al. |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0208340 A1 | 9/2007 | Ganz et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2007/0265616 A1 | 11/2007 | Couture et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0214967 A1 | 9/2008 | Aranyi et al. |
| 2008/0221565 A1 | 9/2008 | Eder et al. |
| 2008/0255642 A1 | 10/2008 | Zarins et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2008/0300588 A1 | 12/2008 | Groth et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0082766 A1 | 3/2009 | Unger et al. |
| 2009/0099582 A1 | 4/2009 | Isaacs et al. |
| 2009/0112229 A1 | 4/2009 | Omori et al. |
| 2009/0125026 A1 | 5/2009 | Rioux et al. |
| 2009/0125027 A1 | 5/2009 | Fischer |
| 2009/0138003 A1 | 5/2009 | Deville et al. |
| 2009/0138006 A1 | 5/2009 | Bales et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0118754 A1 | 5/2011 | Dachs, II et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2011/0301605 A1 | 12/2011 | Horner |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1* | 4/2012 | Davison ............ A61B 18/1445 606/45 |
| 2012/0109186 A1 | 5/2012 | Parrott et al. |
| 2012/0116265 A1 | 5/2012 | Houser et al. |
| 2012/0116379 A1 | 5/2012 | Yates et al. |
| 2012/0116380 A1 | 5/2012 | Madan et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0138660 A1 | 6/2012 | Shelton, IV |
| 2012/0150170 A1 | 6/2012 | Buysse et al. |
| 2012/0150192 A1 | 6/2012 | Dachs, II et al. |
| 2012/0172859 A1 | 7/2012 | Condie et al. |
| 2012/0265196 A1 | 10/2012 | Turner et al. |
| 2012/0265241 A1 | 10/2012 | Hart et al. |
| 2012/0296371 A1 | 11/2012 | Kappus et al. |
| 2012/0323238 A1 | 12/2012 | Tyrrell et al. |
| 2013/0023925 A1 | 1/2013 | Mueller |
| 2013/0030428 A1* | 1/2013 | Worrell ............ A61B 18/1445 606/33 |
| 2013/0030433 A1 | 1/2013 | Heard |
| 2013/0035685 A1 | 2/2013 | Fischer et al. |
| 2013/0079762 A1 | 3/2013 | Twomey et al. |
| 2013/0085496 A1 | 4/2013 | Unger et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0253502 A1 | 9/2013 | Aronow et al. |
| 2013/0338661 A1 | 12/2013 | Behnke, II |

(56) References Cited

U.S. PATENT DOCUMENTS

| | | |
|---|---|---|
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0094801 A1 | 4/2014 | Boudreaux et al. |
| 2014/0194875 A1 | 4/2014 | Reschke et al. |
| 2014/0180281 A1 | 6/2014 | Rusin |
| 2014/0194874 A1 | 7/2014 | Dietz et al. |
| 2014/0194915 A1 | 7/2014 | Johnson et al. |
| 2014/0214019 A1 | 7/2014 | Baxter, III et al. |
| 2014/0228844 A1 | 8/2014 | Hörlle et al. |
| 2014/0257284 A1 | 9/2014 | Artale |
| 2014/0316408 A1 | 10/2014 | Davison et al. |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0133929 A1 | 5/2015 | Evans et al. |
| 2015/0190189 A1 | 7/2015 | Yates et al. |
| 2015/0196352 A1 | 7/2015 | Beckman et al. |
| 2015/0230853 A1 | 8/2015 | Johnson et al. |
| 2015/0265347 A1 | 9/2015 | Yates et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2016/0045248 A1 | 2/2016 | Unger et al. |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0135875 A1 | 5/2016 | Strobl et al. |
| 2016/0157927 A1 | 6/2016 | Corbett et al. |
| 2016/0175024 A1 | 6/2016 | Yates et al. |
| 2016/0175028 A1 | 6/2016 | Trees et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |
| 2016/0199123 A1 | 7/2016 | Thomas et al. |
| 2016/0199125 A1 | 7/2016 | Jones |
| 2016/0228171 A1 | 8/2016 | Boudreaux |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296268 A1 | 10/2016 | Gee et al. |
| 2016/0296270 A1 | 10/2016 | Strobl et al. |
| 2016/0296271 A1 | 10/2016 | Danziger et al. |
| 2016/0302844 A1 | 10/2016 | Strobl et al. |
| 2016/0317215 A1 | 11/2016 | Worrell et al. |

FOREIGN PATENT DOCUMENTS

| | | |
|---|---|---|
| DE | 19608716 C1 | 4/1997 |
| DE | 29623113 U1 | 10/1997 |
| DE | 20004812 U1 | 9/2000 |
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0557806 B1 | 5/1998 |
| EP | 0640317 B1 | 9/1999 |
| EP | 0722696 B1 | 12/2002 |
| EP | 1293172 B1 | 4/2006 |
| EP | 0875209 B1 | 5/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1435852 B1 | 12/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1510178 B1 | 6/2011 |
| EP | 1728475 B1 | 8/2011 |
| EP | 2353518 A1 | 8/2011 |
| EP | 1767164 B1 | 1/2013 |
| EP | 2316359 B1 | 3/2013 |
| EP | 2578172 A2 | 4/2013 |
| EP | 2508143 B1 | 2/2014 |
| GB | 2472216 A | 2/2011 |
| JP | H 08-229050 | 9/1996 |
| JP | 2008-018226 A | 1/2008 |
| JP | 5714508 B2 | 5/2015 |
| WO | WO 81/03272 A1 | 11/1981 |
| WO | WO 93/07817 A1 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/062241 A1 | 8/2002 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/078051 A2 | 9/2004 |
| WO | WO 2004/112618 A2 | 12/2004 |
| WO | WO 2005/052959 A2 | 6/2005 |
| WO | WO 2006/021269 A1 | 3/2006 |

(56) References Cited

FOREIGN PATENT DOCUMENTS

| | | |
|---|---|---|
| WO | WO 2006/036706 A1 | 4/2006 |
| WO | WO 2006/055166 A2 | 5/2006 |
| WO | WO 2006/119139 A2 | 11/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/084768 A1 | 7/2011 |
| WO | WO 2011/089717 A1 | 7/2011 |
| WO | WO 2011/144911 A1 | 11/2011 |
| WO | WO 2012/044606 A2 | 4/2012 |
| WO | WO 2012/166510 A1 | 12/2012 |
| WO | WO 2013/034629 A1 | 3/2013 |
| WO | WO 2013/062978 A2 | 5/2013 |
| WO | WO 2013/102602 A2 | 7/2013 |
| WO | WO 2013/154157 A1 | 10/2013 |
| WO | WO 2015/197395 A8 | 12/2015 |

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, Engineering Formulas § Z.7 (7th ed. 1997).

National Semiconductors Temperature Sensor Handbook—http://www.national.com/appinfo/tempsensors/files/temphb.pdf; accessed online: Apr. 1, 2011.

Glaser and Subak-Sharpe, Integrated Circuit Engineering, Addison-Wesley Publishing, Reading, MA (1979).

Wright, et al., "Time-Temperature Equivalence of Heat-Induced Changes in Cells and Proteins," Feb. 1998. ASME Journal of Biomechanical Engineering, vol. 120, pp. 22-26.

Covidien Brochure, [Value Analysis Brief], LigaSure Advance™ Pistol Grip, dated Rev. Apr. 2010 (7 pages).

Covidien Brochure, LigaSure Impact™ Instrument LF4318, dated Feb. 2013 (3 pages).

Covidien Brochure, LigaSure Atlas™ Hand Switching Instruments, dated Dec. 2008 (2 pages).

Covidien Brochure, The LigaSure™ 5 mm Blunt Tip Sealer/Divider Family, dated Apr. 2013 (2 pages).

Covidien Brochure, The LigaSure Precise™ Instrument, dated Mar. 2011 (2 pages).

Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_VIO_200_S_D027541.

Jang, J. et al. "Neuro-fuzzy and Soft Computing." Prentice Hall, 1997, pp. 13-89, 199-293, 335-393,453-496, 535-549.

Douglas, S.C. "Introduction to Adaptive Filter". Digital Signal Processing Handbook. Ed. Vijay K. Madisetti and Douglas B. Williams. Boca Raton: CRC Press LLC, 1999.

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Sullivan, "Optimal Choice for Number of Strands in a Litz-Wire Transformer Winding," IEEE Transactions on Power Electronics, vol. 14, No. 2, Mar. 1999, pp. 283-291.

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

U.S. Appl. No. 12/576,529, filed Oct. 9, 2009.
U.S. Appl. No. 15/265,293, filed Sep. 14, 2016.
U.S. Appl. No. 15/258,570, filed Sep. 7, 2016.
U.S. Appl. No. 15/258,578, filed Sep. 7, 2016.
U.S. Appl. No. 15/258,586, filed Sep. 7, 2016.
U.S. Appl. No. 15/258,598, filed Sep. 7, 2016.
International Preliminary Report on Patentability, Application No. PCT/US2015/044210, dated Feb. 28, 2017 (7 pages).

* cited by examiner

SIMULTANEOUS I-BEAM AND SPRING DRIVEN CAM JAW CLOSURE MECHANISM

The present disclosure is related generally to electrosurgical devices with various mechanisms for clamping and treating tissue. In particular, the present disclosure is related to electrosurgical devices with simultaneous I-beam and spring driven cam jaw closure mechanism.

Conventional electrosurgical devices have poor grasping and cannot seal without cutting. These issues are due to the fact that the I-beam closes the jaws. Due to component tolerances it is almost impossible to make a set of large jaws that can be closed with an I-beam where the jaws will come fully together with the I-beam closing from the rear of the jaws. The I-beam, however, has lots of advantages on sealing thick and diseased tissue. So, a solution is needed that allows for improved grasping and sealing without cutting, but also allows the jaws to be closed with an I-beam.

While several devices have been made and used, it is believed that no one prior to the inventors has made or used the device described in the appended claims.

CROSS-REFERENCE TO RELATED APPLICATIONS

This application is related to U.S. patent application Ser. No. 14/468,037, titled "LOCKOUT DISABLING MECHANISM," filed Aug. 25, 2014, now U.S. Pub. No. 2016/0051317 and U.S. patent application Ser. No. 14/467,990, titled "ELECTROSURGICAL ELECTRODE MECHANISM," filed Aug. 25, 2014, now U.S. Pub. No. 2016/0051316; each of which is incorporated herein by reference in its entirety.

SUMMARY

In one embodiment, a surgical instrument is provided. The surgical instrument comprises an end effector and a handle assembly. The end effector comprises a movable jaw; and a cutting element slidably movable within the end effector. The handle assembly comprises an energy button configured to deliver energy to at least one electrode located in the end effector; a trigger plate operably coupled to a jaw closure mechanism. The trigger plate configured to close the movable jaw; a firing plate operably coupled to a cutting element drive mechanism. The firing plate is configured to drive the cutting element independently of the jaw closure mechanism. The cutting element drive mechanism is configured to close the movable jaw when the cutting element is driven. The handle assembly also comprises a trigger operatively coupled to the trigger plate and the firing plate. The jaw closure mechanism and the cutting element drive mechanism are configured to simultaneously close the movable jaw.

In another embodiment, the surgical instrument comprises a spring located inline with the jaw closure mechanism, wherein the jaw closure mechanism is configured to close the jaw ahead of the cutting element drive system until a force required to close the movable jaw overcomes a force generated by the spring at which time the cutting element drive mechanism overtakes the jaw closure mechanism to close the movable jaw. In another embodiment, the spring can be pre-compressed to increase the starting load. In another embodiment, the jaw closure mechanism comprises a spring, a closure bar coupled to the spring, and a pivoting link having a proximal end and a distal end, the proximal end coupled to the closure bar and the distal end coupled to the movable jaw. In another embodiment, the surgical instrument comprises a closure actuator coupled to the spring and coupled to the trigger plate via a toggle clamp, wherein the closure actuator is configured to compress the spring.

In another embodiment, the cutting element drive mechanism comprises a firing bar having a proximal end and a distal end, a cutting element coupled to the distal end of the firing bar, a rack coupled to the proximal end of the firing bar, wherein the rack is operatively coupled to the firing plate.

In another embodiment, the surgical instrument comprises a lockout disabling mechanism comprising a lock arm operatively coupled to a lever arm and a lockout element, wherein the lockout element is configured to prevent the cutting element drive mechanism from driving a cutting element.

In one embodiment, a surgical instrument is provided. The surgical instrument comprises an end effector comprising a movable jaw, a cutting element slidably movable within the end effector, a jaw closure mechanism configured to close the movable jaw via a spring driven cam system, and a cutting element drive mechanism configured to drive the cutting element independently of the jaw closure mechanism. The cutting element drive system comprises an I-beam member. The cutting element drive mechanism is configured to close the movable jaw when the cutting element is driven. The jaw closure mechanism and the cutting element drive mechanism are configured to simultaneously close the movable jaw.

In another embodiment, the jaw closure mechanism is configured to close the jaw ahead of the cutting element drive system until a force required to close the movable jaw overcomes a force generated by the spring at which time the cutting element drive mechanism overtakes the jaw closure mechanism to close the movable jaw.

In another embodiment, the spring can be pre-compressed to increase the starting load.

In another embodiment the jaw closure mechanism comprises a closure bar coupled to the spring and a pivoting link having a proximal end and a distal end, the proximal end coupled to the closure bar and the distal end coupled to the movable jaw.

In another embodiment, the surgical instrument comprises a closure actuator having a proximal end and a distal end, the distal end coupled to the spring and the proximal end coupled to a toggle clamp configured to drive the closure actuator. The closure actuator is configured to compress the spring when the closure actuator moves in a distal direction.

In another embodiment, the cutting element drive mechanism comprises a firing bar having a proximal end and a distal end, a cutting element coupled to the distal end of the firing bar, and a rack coupled to the proximal end of the firing bar. The rack is operatively coupled to the firing plate.

In another embodiment, the surgical instrument comprises a lockout disabling mechanism comprising a lock arm operatively coupled to a lever arm and a lockout element. The lockout element is configured to prevent the cutting element drive mechanism from driving a cutting element.

In one embodiment, a surgical instrument is provided. The surgical instrument comprises a handle assembly, a shaft assembly, and an end effector. The handle assembly comprises a trigger operatively coupled to a trigger plate and a firing plate, an energy button configured to deliver energy to at least one electrode, a lockout element operatively coupled to the energy button. The lockout element is configured to prevent operation of the firing plate. The handle assembly also comprises a lockout disabling mechanism configured to disable the lockout element. The lockout disabling mechanism is operable between a first position and a second position. When the lockout disabling mechanism is located in the first position, the lockout element is enabled and can be unlocked by the energy button, and wherein when the lockout disabling mechanism is in the second position, the lockout element is disabled. The shaft assembly comprises a proximal end and a distal end. The shaft assembly is coupled to the handle assembly at the proximal end. The end effector is coupled to the distal end of the shaft assembly. The end effector comprises a jaw assembly, comprising a first jaw member and a second jaw member. The rotation of the trigger plate transitions the jaw assembly between an open configuration and an approximated configuration by moving at least one of the first jaw member and the second jaw member relative to the other one of the first jaw member and the second jaw member. The end effector also comprises a cutting element deployable in response to rotation of the firing plate, a jaw closure mechanism configured to close the movable jaw via a spring driven cam system, and a cutting element drive mechanism configured to drive the cutting element independently of the jaw closure mechanism. The cutting element drive system comprises an I-beam member. The cutting element drive mechanism is configured to close the movable jaw when the cutting element is driven. The jaw closure mechanism and the cutting element drive mechanism are configured to simultaneously close the at least one of the first jaw member and the second jaw member.

In another embodiment, the jaw closure mechanism is configured to close the jaw ahead of the cutting element drive system until a force required to close the at least one of the first jaw member and the second jaw member overcomes a force generated by the spring at which time the cutting element drive mechanism overtakes the jaw closure mechanism to close the at least one of the first jaw member and the second jaw member.

In another embodiment, the spring can be pre-compressed to increase the starting load.

In another embodiment, the jaw closure mechanism comprises a closure bar coupled to the spring and a pivoting link having a proximal end and a distal end, the proximal end coupled to the closure bar and the distal end coupled to the at least one of the first jaw member and the second jaw member.

In another embodiment, the surgical instrument comprises a closure actuator having a proximal end and a distal end, the distal end coupled to the spring and the proximal end coupled to a toggle clamp configured to drive the closure actuator, wherein the closure actuator is configured to compress the spring when the closure actuator moves in a distal direction.

In another embodiment, the cutting element drive mechanism comprises a firing bar having a proximal end and a distal end a cutting element coupled to the distal end of the firing bar and a rack coupled to the proximal end of the firing bar. The rack is operatively coupled to the firing plate.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the embodiments described herein are set forth with particularity in the appended claims. The embodiments, however, both as to organization and methods of operation may be better understood by reference to the following description, taken in conjunction with the accompanying drawings as follows.

DESCRIPTION

Figure 1:
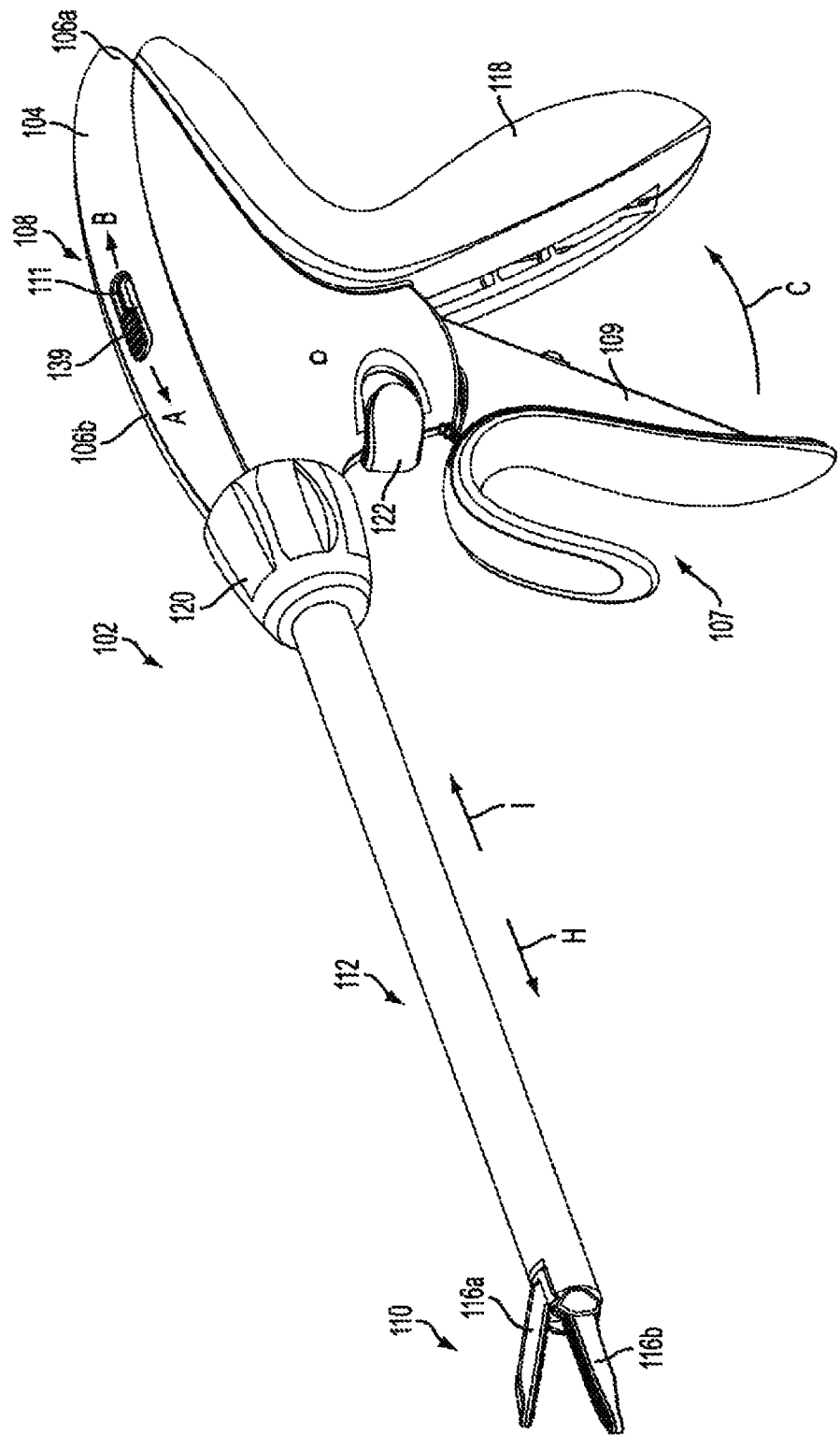
FIG. 1 illustrates a surgical instrument comprising a knife lockout disabling mechanism, according to one embodiment.

In the following detailed description, reference is made to the accompanying drawings, which form a part hereof. In the drawings, similar symbols and reference characters typically identify similar components throughout the several views, unless context dictates otherwise. The illustrative embodiments described in the detailed description, drawings, and claims are not meant to be limiting. Other embodiments may be utilized, and other changes may be made, without departing from the scope of the subject matter presented here.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Before explaining the various embodiments of the surgical devices having a closure system comprising an I-beam and spring driven cam system to simultaneously close a set of opposing jaws in detail, it should be noted that the various embodiments disclosed herein are not limited in their application or use to the details of construction and arrangement of parts illustrated in the accompanying drawings and description. Rather, the disclosed embodiments may be positioned or incorporated in other embodiments, variations and modifications thereof, and may be practiced or carried out in various ways. Accordingly, embodiments of the surgical devices disclosed herein are illustrative in nature and are not meant to limit the scope or application thereof. Furthermore, unless otherwise indicated, the terms and expressions employed herein have been chosen for the purpose of describing the embodiments for the convenience of the reader and are not to limit the scope thereof. In addition, it should be understood that any one or more of the disclosed embodiments, expressions of embodiments, and/or examples thereof, can be combined with any one or more of the other disclosed embodiments, expressions of embodiments, and/or examples thereof, without limitation.

Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

In various embodiments, the present disclosure provides an electrosurgical instrument having a closure system comprising an I-beam and spring driven cam system to simultaneously close a set of opposing jaws. In order to grasp better a separate mechanism is provided to close the jaws independently of the I-beam drive. To ensure the I-beam will also be able to close the jaws the separate mechanism operates in tandem with the I-beam drive. In one embodiment, a cam closure that closes the jaws and moves along with the I-beam is provided. Some conventional electrosurgical devices employ a toggle clamp to move the I-beam to close the jaws. A separate closure system can be attached to the toggle clamp alongside the I-beam so that they both move at the same time. The cam closure can be timed to close the jaws before the I-beam. The cam system also can incorporate an inline spring. This spring can compress at the end of the closure stroke to keep the jaws shut with a set spring force. If material in the jaws forces the spring to compress too much on the cam closure then the I-beam can take over to close the jaws. Accordingly, in this system the I-beam will ensure the jaws always fully close the jaws with the toggle clamp. The I-beam is configured to only close the jaws when the material in the jaws takes more force to close than the cam spring can provide. The cam system also can have a rising mechanical advantage as the jaw is closed such that the further the spring is compressed the less force is exerted on the jaws. This prevents damaging tissue from too much spring force.

In one embodiment, the closure system comprising an I-beam and spring driven cam system to simultaneously close a set of opposing jaws can be configured to operate in the following manner: (1) place tissue in the jaws and pull the trigger; (2) the toggle clamp pushes on the I-beam and the cam closure; (3) the cam immediately pushes on the jaw through a spring to close it, the I-beam trails a closure ramp on the upper jaw; (4) the cam fully closes the jaws before the toggle stops moving; (5) the toggle clamp continues to move (e.g., another 0.05 inches) to compress the closure spring to ensure the jaws are sprung closed, the I-beam moves over the top of the ramp; and (6) thick tissue in the jaws may compress the spring on the cam closure before the end of the toggle stroke, the I-beam will hit the closure ramp and force the jaws closed to ensure that the I-beam will repeatedly be located over the ramp with the jaws closed before the toggle stops moving.

The closure system comprising an I-beam and spring cam driven cam system is configured to simultaneously close a set of opposing jaws provides several advantages over conventional devices. The disclosed device can seal tissue without necessarily cutting the tissue, provides improved tissue grasping, ensures that the I-beam is located over the ramp before a gear train in the jaw device takes over to provide lower force to fire. The disclosed closure system also provides improved jaw opening and tissue dissection over conventional devices. The disclosed closure system also provides lower force to fire from preload on tissue. The gears fire the I-beam forward and can be configured to operate with conventional electrosurgical jaw designs. Additional advantages, not necessarily described herein, are also provided.

In various embodiments, the present disclosure provides an electrosurgical radio frequency (RF) bipolar sealing device comprising an I-beam and spring driven cam system to simultaneously close a set of opposing jaws. The spring driven cam closure system can close the jaws first unless the force to close the jaws overcomes the spring, at this point the I-beam will close the jaws. The cam system composes a spring connected to a bar, which is in turn connected to a pivoting link, which is then connected to a jaw. Pushing on the spring pushes on the bar which pushes on the link which closes the jaw. The spring on the cam closure system can be pre-compressed to raise its starting load.

Turning now to the figures, FIG. 1 illustrates a surgical instrument 102 comprising a trigger assembly 107 and a closure system arrangement for closing the jaws 110 comprising a separate spring driven cam closure mechanism that is independent of the I-beam closure mechanism. The spring driven cam closure system and the I-beam closure system are configured to independently close a set of opposing jaws 116a, 116b, and independently fire a cutting element in the end effector 110. The trigger assembly 107 is configured to clamp and independently fire an end effector 110 coupled to the shaft assembly 112 of the surgical instrument 102. In the embodiment shown in FIG. 1, the surgical instrument comprises a trigger assembly 107 and a lockout disabling mechanism 108. In this view, a first jaw member 116a of an end effector 110 is fully open and the knife lockout disabling mechanism 108 is located in the off position. The knife lockout disabling mechanism 108 is configured to clamp and fire an end effector 110 coupled to the surgical instrument 102. The surgical instrument 102 comprises a handle assembly 104, a shaft assembly 112, and the end effector 110. The shaft assembly 112 comprises a proximal end and a distal end. The proximal end of the shaft assembly 112 is coupled to the distal end of the handle assembly 104. The end effector 110 is coupled to the distal end of the shaft assembly 112. The handle assembly 104 comprises a pistol grip 118. The handle assembly 104 comprises a left handle housing shroud 106a and a right handle housing shroud 106b. The trigger assembly 107 comprises a trigger 109 actuatable towards the pistol grip 118. The knife lockout disabling mechanism 108 comprises a button 139, or knob, that is actuatable for adjusting or controlling the position of the knife lockout disabling mechanism 108 between first and second positions A and B (A=Distal and B=Proximal relative to the clinician) within a slot 111 formed in the left handle housing shroud 106a. A rotatable shaft knob 120 is configured to rotate the shaft assembly 112 with respect to the handle assembly 104. The handle assembly 104 further comprises an energy button 122 configured to provide electrosurgical energy to one or more electrodes in the end effector 110.

The knife lockout mechanism forces the user to first clamp (close the jaws 110), energize the electrodes, then cut the tissue (fire the knife). The knife unlock feature contains the energy button 122 so that the energy button 122 has to be depressed before the knife can be released or that the single trigger can move the rack 136 forward. The single trigger 109 closes the jaws in the first ~13 degrees of stroke. The single trigger 109 fires the knife in the last ~29 degrees of stroke. The lockout is the stop in between the first stroke and the second stroke. An energy switch (not shown) is located underneath the energy button 122 housing. Accordingly, the lock release mechanism also is the energy delivery element.

The shaft assembly 112 comprises a closure/jaw actuator, a firing/cutting member actuator, and an outer sheath. In some embodiments, the outer sheath comprises the closure actuator. The outer sheath comprises one or more contact electrodes on a distal end configured to interface with the end effector 110. The one or more contact electrodes are operatively coupled to the energy button 122 and an energy source (not shown).

The energy source may be suitable for therapeutic tissue treatment, tissue cauterization/sealing, as well as sub-therapeutic treatment and measurement. The energy button 122 controls the delivery of energy to the electrodes. As used throughout this disclosure, a button refers to a switch mechanism for controlling some aspect of a machine or a process. The buttons may be made out of a hard material such as usually plastic or metal. The surface may be formed or shaped to accommodate the human finger or hand, so as to be easily depressed or pushed. Buttons can be most often biased switches, even though many un-biased buttons (due to their physical nature) require a spring to return to their un-pushed state. Terms for the "pushing" of the button, may include press, depress, mash, and punch.

In some embodiments, an end effector 110 is coupled to the distal end of the shaft assembly 112. The end effector 110 comprises a first jaw member 116a and a second jaw member 116b. The first jaw member 116a is pivotally coupled to the second jaw member 116b. The first jaw member 116a is pivotally moveable with respect to the second jaw member 116b to grasp tissue therebetween. In some embodiments, the second jaw member 116b is fixed. In other embodiments, the first jaw member 116a and the second jaw member 116b are pivotally movable. The end effector 110 comprises at least one electrode. The electrode is configured to deliver energy. Energy delivered by the electrode may comprise, for example, radiofrequency (RF) energy, sub-therapeutic RF energy, ultrasonic energy, and/or other suitable forms of energy. In some embodiments, a cutting member (not shown) is receivable within a longitudinal slot defined by the first jaw member 116a and/or the second jaw member 116b. The cutting member is configured to cut tissue grasped between the first jaw member 116a and the second jaw member 116b. In some embodiments, the cutting member comprises an electrode for delivering energy, such as, for example, RF and/or ultrasonic energy.

In certain instances, as described above, the surgical instrument 102 may include an automatic energy lockout mechanism. The energy lockout mechanism can be associated with a closure mechanism of the surgical instrument 102. In certain instances, the energy lockout mechanism can be configured to permit energy delivery to the end effector 10 when the energy delivery button 122 is actuated if the jaw members 116a and 116b are in an open configuration. In certain instances, the energy lockout mechanism may be configured to deny energy delivery to the end effector 110 when the energy delivery button 122 is actuated if the jaw members 116a and 116b are in a closed configuration. In certain instances, the energy lockout mechanism automatically transitions from permitting the energy delivery to denying the energy delivery when the jaw members 116a and 116b are transitioned from the closed configuration to the open configuration, for example. In certain instances, the energy lockout mechanism automatically transitions from denying the energy delivery to permitting the energy delivery when the jaw members 116a and 116b are transitioned from the open configuration to the closed configuration, for example.

Figure 2:
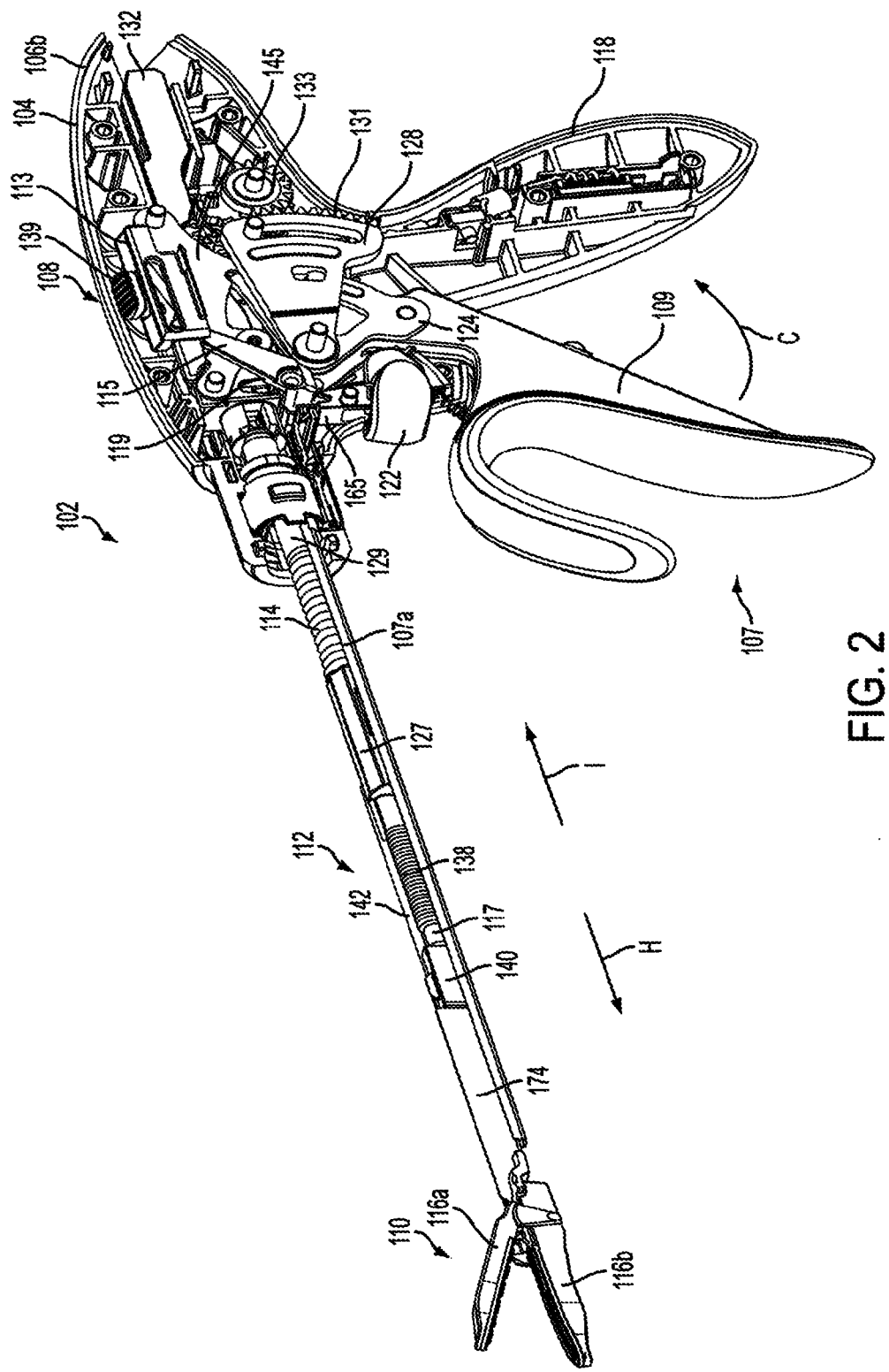
FIG. 2 is a perspective view of a handle assembly of the surgical instrument illustrated in FIG. 1 with the left handle housing shroud and several sheaths in the shaft assembly removed, according to one embodiment.

FIG. 2 is a perspective view of a handle assembly 104 of a surgical instrument 102 illustrated in FIG. 1, according to one embodiment, with the right housing shroud 106a and the outer and inner sheaths of the shaft assembly 112 removed to show some of the internal mechanisms. The left handle housing shroud 106b of the handle assembly 104 comprises the knife lockout disabling mechanism 108. The button 139 is located in the first "off" position A (A=distal relative to the clinician) within the slot 111 formed in the right handle housing shroud 106a. In the illustrated embodiment, position B (B=proximal relative to the clinician) corresponds to the second "on" position of the knife lockout disabling mechanism 108, where the knife lockout mechanism remains disabled until the button is switched back to position A. Accordingly, position A corresponds to the enabled state of the knife lockout mechanism and position B corresponds to the disabled state of the knife lockout mechanism. Stated differently, position A corresponds to the "off" state of the knife lockout disabling mechanism 108 and position B corresponds to the "on" state of the knife lockout disabling mechanism 108. When the knife lockout mechanism is in the disabled state, the energy button 122 may appear to be depressed to provide a visual indication to the clinician that the knife lockout mechanism has been disabled but without energizing the electrodes in the end effector 110 (FIG. 1). When the knife lockout mechanism is disabled, the knife may be fired at will without the need to apply electrosurgical energy to one or more electrodes in the end effector 110.

The trigger assembly 107 comprises the necessary components for closing the jaw members 116a, 116b and firing the cutting member or knife bands 174. The trigger assembly 107 comprises a trigger plate 124 and firing plate 128 operatively coupled to the trigger 109. Squeezing the trigger 109 in direction C towards the pistol grip 118 rotates the trigger plate 124 which operates the toggle clamp 145 to advance a yoke 132 and a closure actuator 129 distally to close the jaw members 116a, 116b of the end effector. Initial rotation of the trigger plate 124 also slightly rotates the firing plate 128. The firing plate 128 comprises a sector gear with a plurality of teeth 131 that engage and rotate a first pinion gear 133, which engages a second pinion gear 134 to advance a rack 136 (neither is shown in this view). A lock arm 157 (shown in FIGS. 21-22, for example) is operatively coupled to a lever arm 115, an unlock arm 119, and a lockout element 165. When the instrument 102 is in normal lockout mode, the lock arm 157 engages a notch 158 (shown in FIGS. 4 and 21-23, for example) in the rack 136 to lock the rack 136 and prevent the rack 136 from moving distally (firing) no matter how hard the trigger 109 is squeezed.

The single trigger 109 closes the jaws in the first ~13 degrees of stroke. The trigger plate 124 is configured to interface with the trigger plate 124 during rotation of the trigger 109 from an initial position to a first rotation, which is ~13 degrees of stroke, for example. The trigger plate 124 is operably coupled to the firing plate 128. In certain instances, the firing plate 128 may include a first slot 128a and a second slot 128b. The first slot 128a receives a drive pin 148 fixedly coupled to the trigger plate 124. The pin 148 slidably moves within the first slot 128a. Rotation of the trigger plate 124, while the pin 148 is slidably received within the first slot 128a, drives rotation of the firing plate 128. The teeth 131 of the sector gear engage and rotate the first pinion 133, which in turn drives the second pinion 134, which drives the rack 136 distally to fire the cutting element, or knife, but only when the knife lockout is unlocked, released, or disabled.

The single trigger 109 fires the knife in the last ~29 degrees of stroke. Rotation of the trigger plate 124 beyond a predetermined rotation such as, for example, the first rotation, causes rotation of the firing plate 128. Rotation of the firing plate 128 deploys a cutting member within the end effector 110. For example, in the illustrated embodiment, the firing plate 128 comprises a sector gear operably coupled to a rack 136 through the first and second pinions 133, 134. The firing plate 128 comprises a plurality of teeth 131 configured to interface with the first pinion 133. Rotation of the firing plate 128 rotates the first and second pinions 133, 134, to drive the rack 136 distally. Distal movement of the rack 136 drives the cutting member actuator distally, causing deployment of the cutting member (e.g., knife) within the end effector 110.

The lockout is the stop in between the first stroke and the second stroke. Turning back now to the description of the lockout disabling mechanism 108, when the slider 113 button 139 portion is in located in position A, the lock arm 157 cam be released by pressing or actuating the energy button 122 to rotate the lockout element 165, which rotates the unlock arm 119 to release the lock arm 157. Once the lock arm 157 is released, the rack 136 is enabled to advance distally and fire the knife by squeezing the trigger 109 in direction C further towards the pistol grip 118. As the trigger 109 is squeezed, the firing plate 128 rotates and drives the first pinion gear 133, which drives the second pinion gear 134 to drive the rack 136.

When the button 139 is located in position B, the slider 113 rotates the lever arm 115, which rotates the unlock arm 119 to releases the lock arm 157. While the button 139 is in position B, the rack 136 can be fired without the need to press energy button 122 to rotate the lockout element 165. A detent may be provided to hold the button in either position A or B. These and other features are described in more detail hereinbelow.

The shaft assembly 112 comprises a closure/jaw actuator and a firing/cutting member actuator. The closure/jaw actuator comprises a yoke 132 and toggle clamp 145 assembly operatively coupled to a closure actuator 129 which acts on a closure spring 114 coupled to a spring-to-bar interface element 127 and a closure bar 142. In one instance the closure bar 142 is operatively coupled to the jaw members 116a, 116b via at least one linkage. The firing/cutting member actuator comprises a rack 136 operatively coupled to a firing bar 117, which is slidably received within the closure actuator 129 and the closure spring 114. The firing bar 117 is coupled to a knife pusher block 140 and a flexible I-beam knife band 174 comprising multiple flexible bands fastened together and a cutting element at the distal end. Advancing the rack 136 in the distal direction advances the cutting element band 174 distally through a channel or slot formed in the jaw members 116a, 116b.

Figure 3:
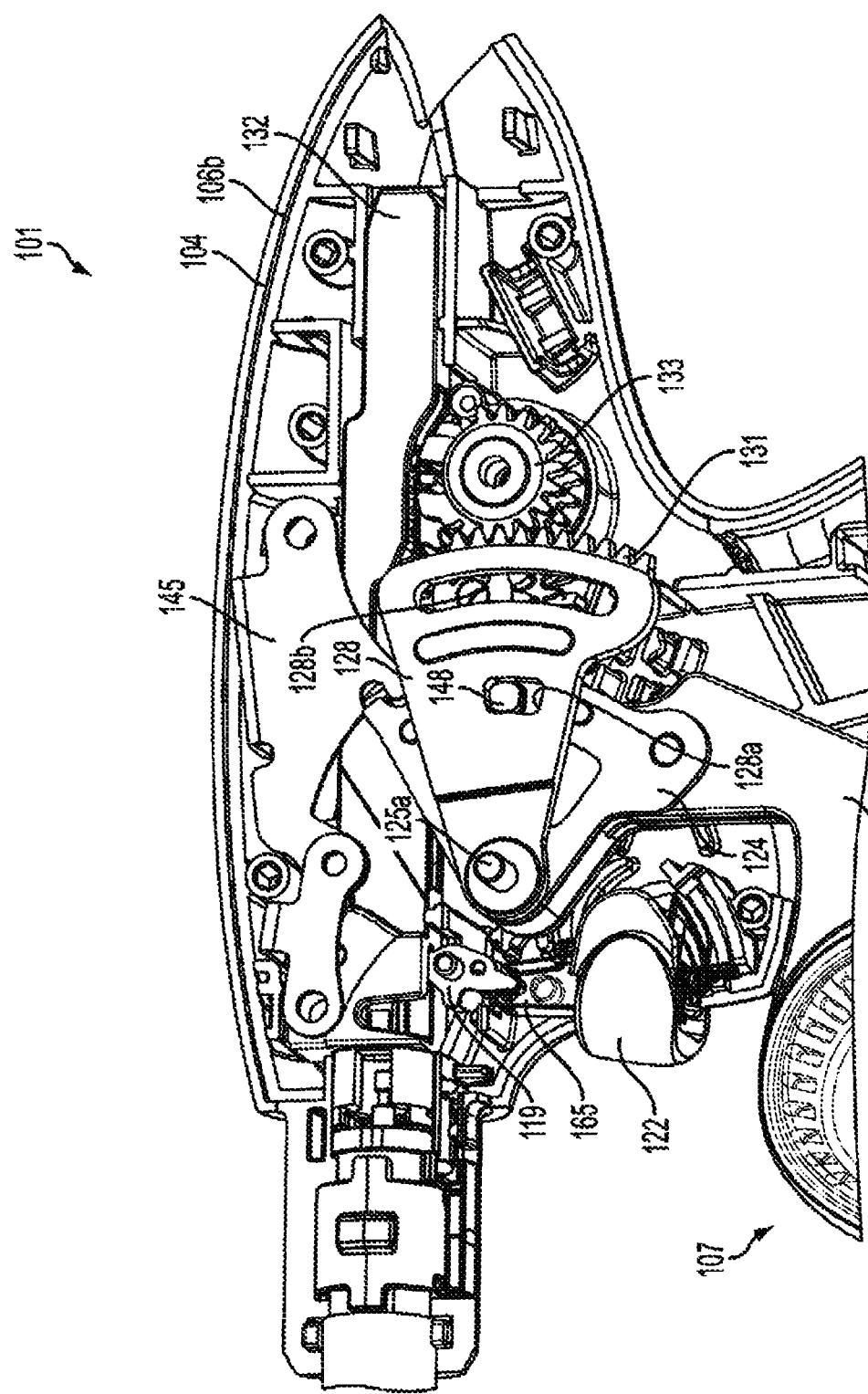
FIG. 3 is a side elevation view of a handle assembly of a surgical instrument, similar to the surgical instrument shown in FIGS. 1 and 2, with the left handle housing shroud removed, and without the lockout disabling mechanism, according to one embodiment.

FIG. 3 is a side elevation view of a handle assembly 104 of a surgical instrument 101, with the left handle housing shroud 106a removed to expose various mechanisms located within the handle assembly 104 and without the knife lockout disabling mechanism 108, according to one embodiment. Except for the knife lockout disabling mechanism, in other aspects, the surgical instrument 101 operates in a manner similar to the surgical instrument described in connection with FIGS. 1 and 2.

Figure 4:
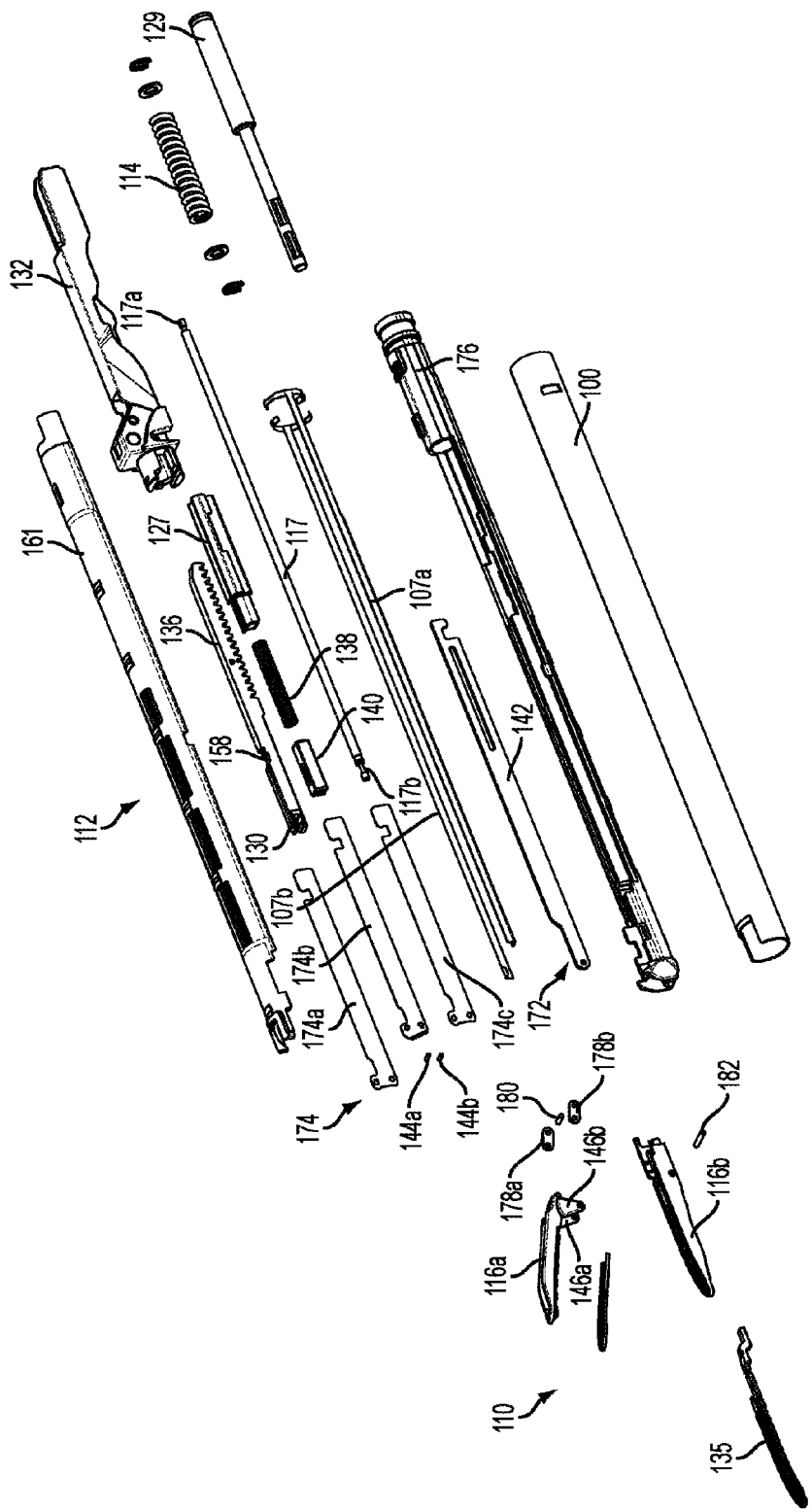
FIG. 4 is an exploded view of the shaft assembly, end effector, yoke, and rack portions of the surgical instrument shown in FIGS. 1 and 2, according to one embodiment.
Figure 5:
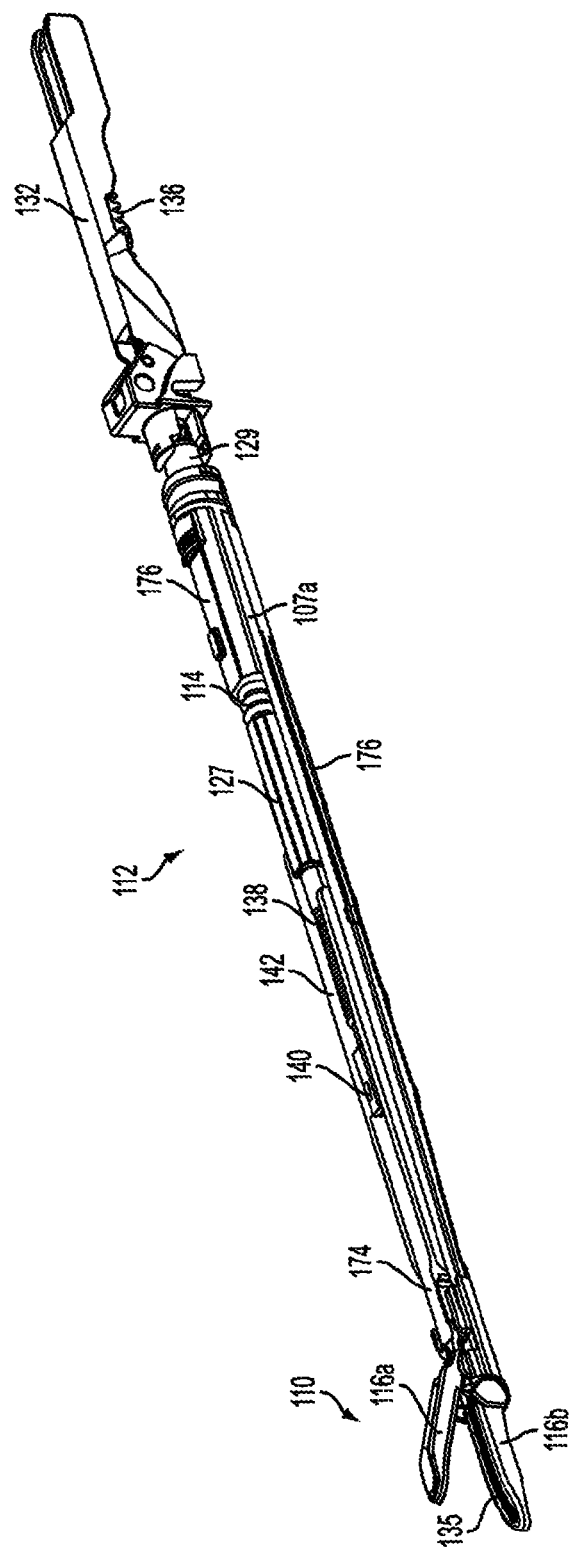
FIG. 5 is a perspective view of the shaft assembly, end effector, yoke, and rack shown in FIG. 4 in the assembled state, according to one embodiment.
Figure 6:
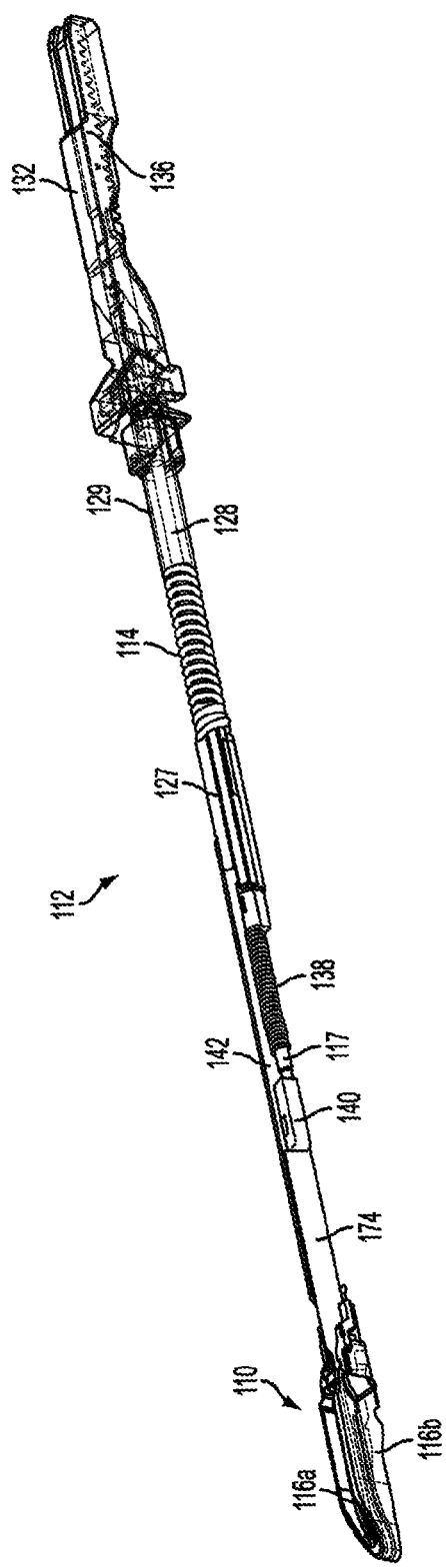
FIG. 6 is a perspective view of the shaft assembly, end effector, yoke, and rack shown in FIG. 5, according to one embodiment, with the electrically insulative nonconductive tube removed to show the functional components of the shaft assembly in the assembled state.
Figure 7:
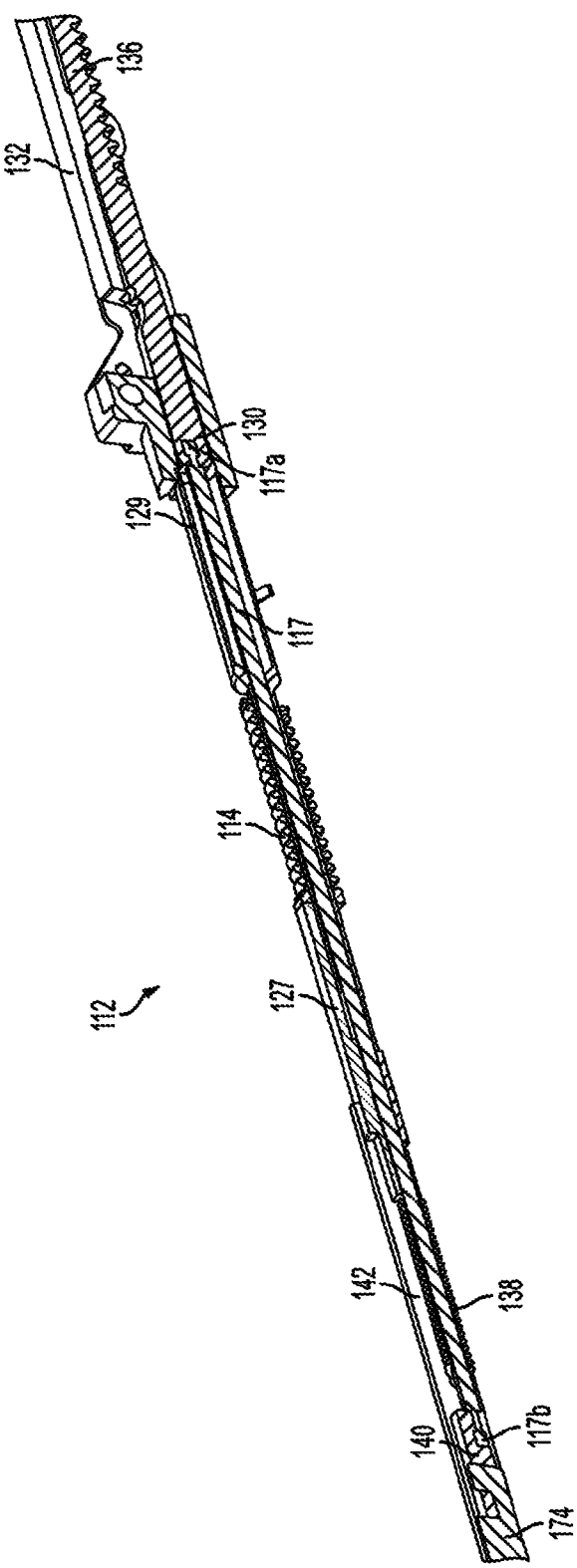
FIG. 7 is a sectional view taken along a longitudinal axis of the shaft assembly, yoke, and rack shown in FIG. 5, according to one embodiment, to show the functional components of the shaft assembly in the assembled state.
Figure 8:
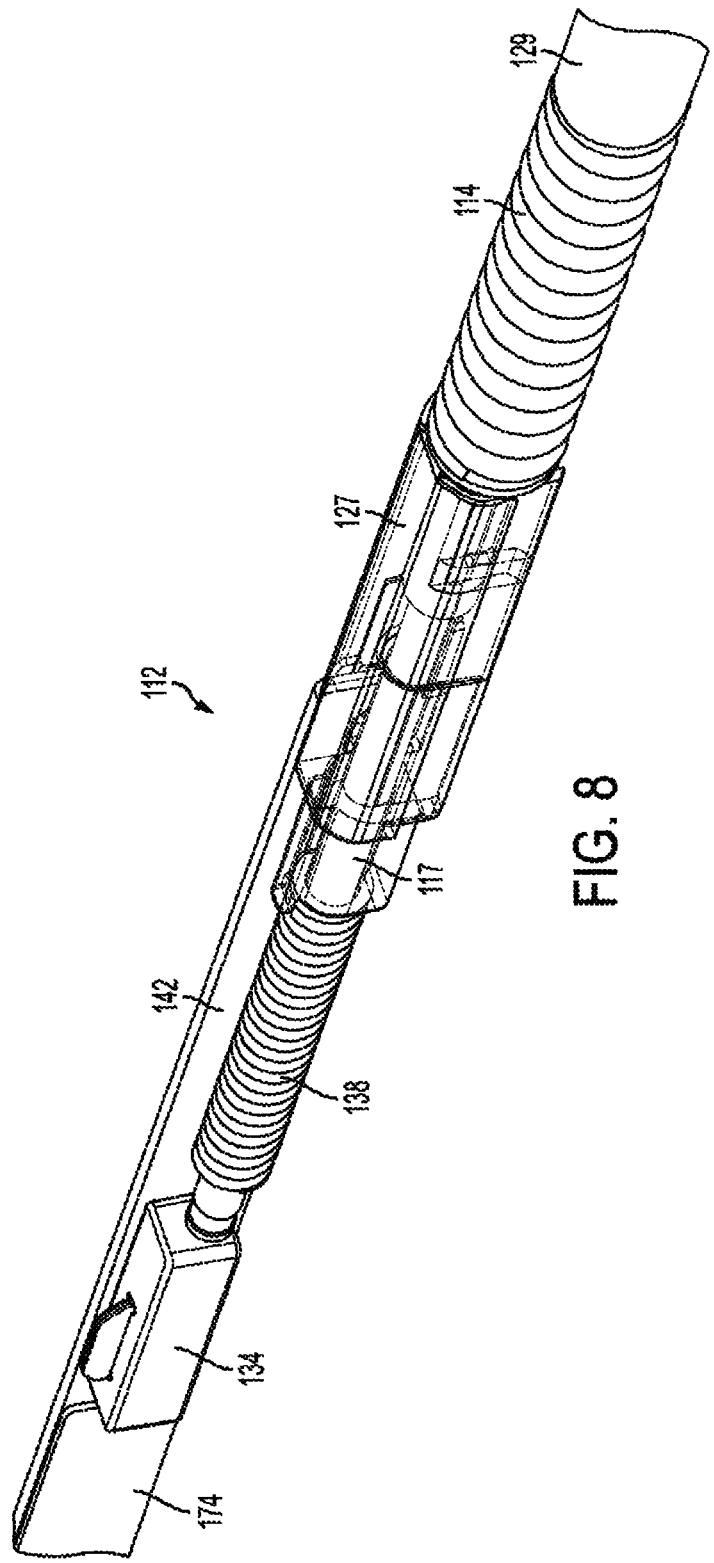
FIG. 8 is partial perspective view of the shaft assembly shown in FIG. 7, according to one embodiment.

FIG. 4 is an exploded view of the shaft assembly 112, end effector 110, yoke 132, and rack 136 portions of the surgical instrument 102 shown in FIGS. 1 and 2, according to one embodiment. FIG. 5 is a perspective view of the shaft assembly 112, end effector 110, yoke 132, and rack 136 shown in FIG. 4 in the assembled state, according to one embodiment. FIG. 6 is a perspective view of the shaft assembly 112, end effector 110, yoke 132, and rack 136 shown in FIG. 5, according to one embodiment, with the electrically insulative nonconductive tube 176 removed to show the functional components of the shaft assembly 112 in the assembled state. FIG. 7 is a sectional view taken along a longitudinal axis of the shaft assembly 112, yoke 132, and rack 136 shown in FIG. 5, according to one embodiment, to show the functional components of the shaft assembly 112 in the assembled state. FIG. 8 is partial perspective view of the shaft assembly 112 shown in FIG. 7, according to one embodiment.

With reference now to FIGS. 4-7, the shaft assembly 112 comprises an outer tube 100 which contains or houses the various functional components of the shaft assembly 112. An electrically insulative nonconductive tube 176 is slidably received within the outer tube 100. A clamp tube 161 is attached to the nonconductive tube 176. The functional components of the shaft assembly 112 are slidably contained within the within the nonconductive tube 176 whereas the conductive elements 107a, 107b employed to supply electrical energy to the end effector 110 electrodes 135 are located outside the nonconductive tube 176. A closure actuator 129 is coupled to the distal end of the yoke 132. The closure actuator 129 comprises a proximal portion and a distal portion. The distal portion of the closure actuator 129 is sized to be received within a closure spring 114. The proximal portion of the closure actuator 129 is sized to compress the closure spring 114. The closure spring 114 is coupled to a closure bar 142 through a spring to bar interface element 127. The distal end 172 of the closure bar 142 is operatively coupled to the jaws 116a, 116b by a pin 180 and closure linkages 178a, 178b. The jaws 116a, 116b are pivotally coupled by a pin 182 and rotatable support structures 146a, 146b formed in the top jaw 116a. The closure actuator 129 is coupled to the distal end of the yoke 132, which is operatively coupled to the toggle clamp 145 (FIGS. 1-3, for example). As previously described, the toggle clamp 145 is movably coupled to the trigger plate 124 (FIGS. 1-3), for example. Rotation of the trigger plate 124 straightens the toggle clamp 145 to drive the yoke 132 distally. Distal movement of the yoke 132 causes distal movement of the closure actuator 129 to compress the closure spring 114 and drive the closure bar 142. Distal movement of the closure actuator 129 pivotally moves the first jaw member 116a from an open position to a closed position with respect to the second jaw member 116b, for example.

A firing bar 117 comprises a proximal end 117a and a distal end 117b. The proximal end 117a of the firing bar 117 is coupled to the distal end 130 of the rack 136. The rack 136 is received within the yoke 132. The firing bar 117 is received within the closure actuator 129, the spring to bar interface element 127, and the jaw open spring 138. The distal end 117b of the firing bar 117 is fixedly coupled to a knife pusher block 140, which is fixedly coupled to a cutting element 174 (knife). The cutting element 174 comprises flexible bands 174a, 174b, 174c, which are fastened by the knife pusher block 140 at the proximal end and by pins 144a, 144b at the distal end to form knife or cutting element having an I-beam configuration. As previously described, the teeth 131 of the sector gear of the firing plate 128 engage and rotate the pinions 133, 134, which drive the rack 136 distally. The rack 136 drives the firing bar 117, which in turn drives the flexible I-beam cutting element 174 when the lock arm 157 is disengaged from a notch 158 formed in the rack 136.

Figure 9:
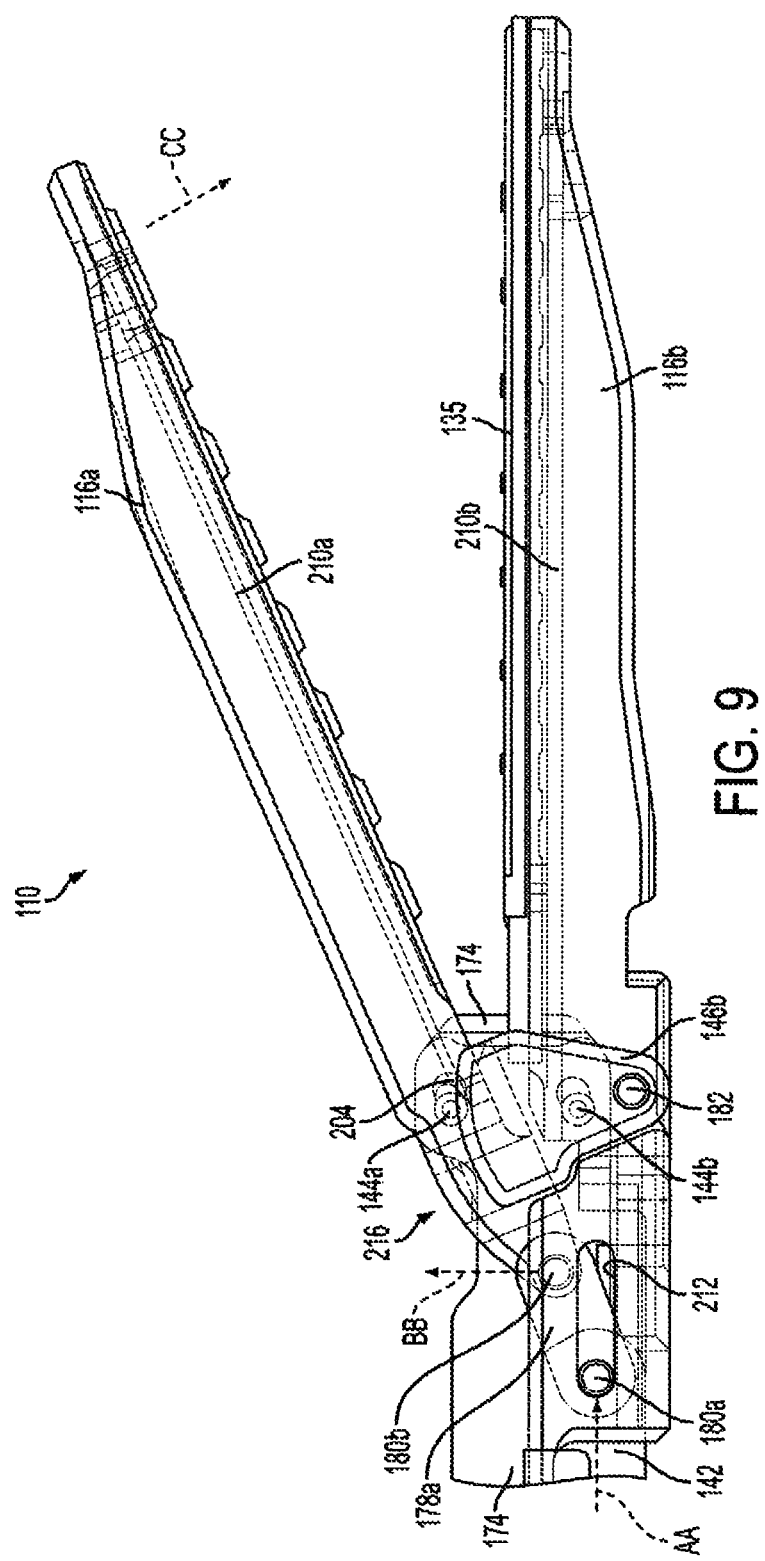
FIG. 9 is a side view of an end effector portion of the surgical instrument shown in FIGS. 1 and 2 with the jaws open, according to one embodiment.

FIG. 9 is a side view of an end effector 110 portion of the surgical instrument 102 shown in FIGS. 1 and 2 with the jaws open, according to one embodiment. The closure bar 142 is operatively coupled to the proximal end of the top jaw 116a via the closure linkages 178a, 178b (not shown) and first and second pins 180a, 180b. The lower pin 180a is slidably movable within a slot 212. As the closure bar 142 moves distally in the direction indicated by arrow AA, the pin 180a slides in the slot 212 to and forces the second pin 180b to move upwardly in the direction indicated by arrow BB to force the top jaw 116a to rotate to a closed position as indicated by arrow CC. The top jaw 116a pivots about a pivot point defined by the fastener pin 182. The bottom jaw 116b comprises the electrode 135, which is electrically coupled to an energy source (e.g., an RF electrosurgical energy source). The flexible I-beam band knife comprises a knife or cutting element 174. The cutting element 174 and the fastener pins 144a, 144b form an I-beam member 216 that forces the jaws 116a, 116b shut when the cutting element 174 is fired by the rack 136 and firing bar 117, as previously described. The I-beam member 216 advances distally on tracks 210a, 210b formed in the respective upper and lower jaws 116a, 116b to force the jaws 116a, 116b shut and compress the tissue located therebetween. A ramp 204 is defined at the proximal end of the top track 210a in the top jaw 116a. Accordingly, a predetermined force is required to advance the I-beam member 216 over the ramp 204 before the I-beam member 216 engages the top track 210a to close the jaws 116a, 16b as the I-beam member 216 is advanced distally by the flexible I-beam band 174. In the present view, the I-beam member 216 is located behind the ramp 204 as the linkages 178a, 178b (not shown) close the jaws 116a, 116b.

Figure 10:
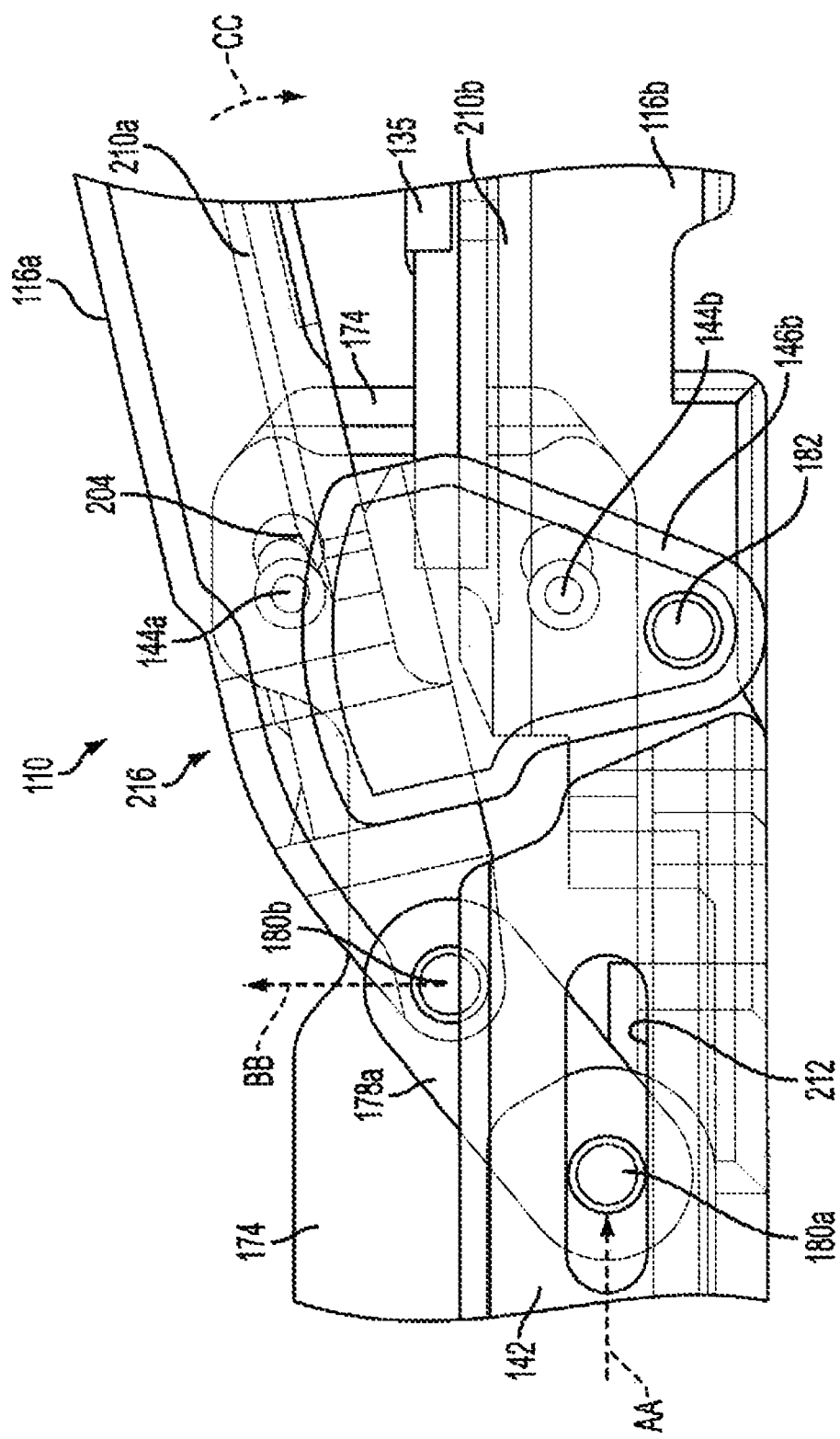
FIG. 10 shows the closure bar and I-beam member at the initial stage of clamp closure and firing sequence where the I-beam member is located at the base of a ramp in the upper jaw, according to one embodiment.

FIGS. 10-13 illustrate a sequence of firing the I-beam member 216 and closure spring 114 driven cam system to simultaneously close a set of opposing jaws 116a, 116b. FIG. 10 shows the closure bar 142 and the I-beam member 216 at the initial stage of clamp closure and firing sequence where the I-beam member 216 is located behind or at the base of a ramp 204 in the upper jaw 116a, according to one embodiment. The pins 144a, 144b (not shown) of the I-beam member 216 are located at the base of the ramp 204 prior to firing the cutting element 174. In this view, the I-beam member 216 is located behind the ramp 204 as pivoting link 178a closes the upper jaw 116a in direction CC.

Figure 11:
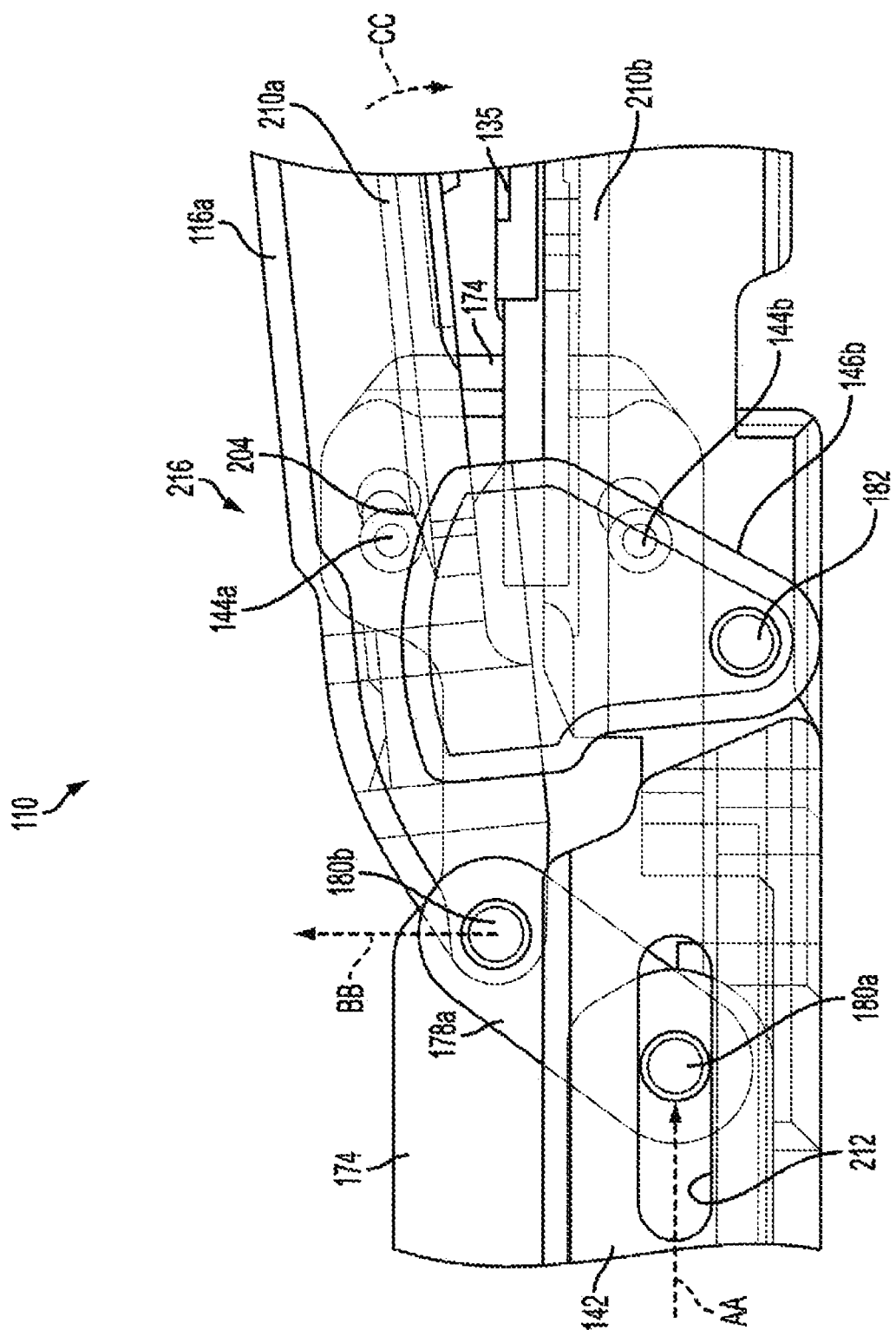
FIG. 11 shows the closure bar and I-beam member further advanced distally than shown in FIG. 10, where the I-beam member is located at an intermediate position along the ramp in the upper jaw, according to one embodiment.

FIG. 11 shows the closure bar 142 and I-beam member 216 further advanced distally in direction AA than shown in FIG. 10, where the I-beam member 216 is located at an intermediate position along the ramp 204 in the upper jaw 116a, according to one embodiment. FIG. 11 shows the closure bar 142 pushing on the bottom pin 180a to move distally in direction AA within the slot 212. In response, the pivoting link 178a moves distally in direction AA and rotates counterclockwise pushing the top pin 180b upwardly in direction BB to apply a closing force to the upper jaw 116a. The I-beam member 216 also advances partially up the ramp 204. The upper jaw 116a rotates slightly in direction CC toward a closed position.

Figure 12:
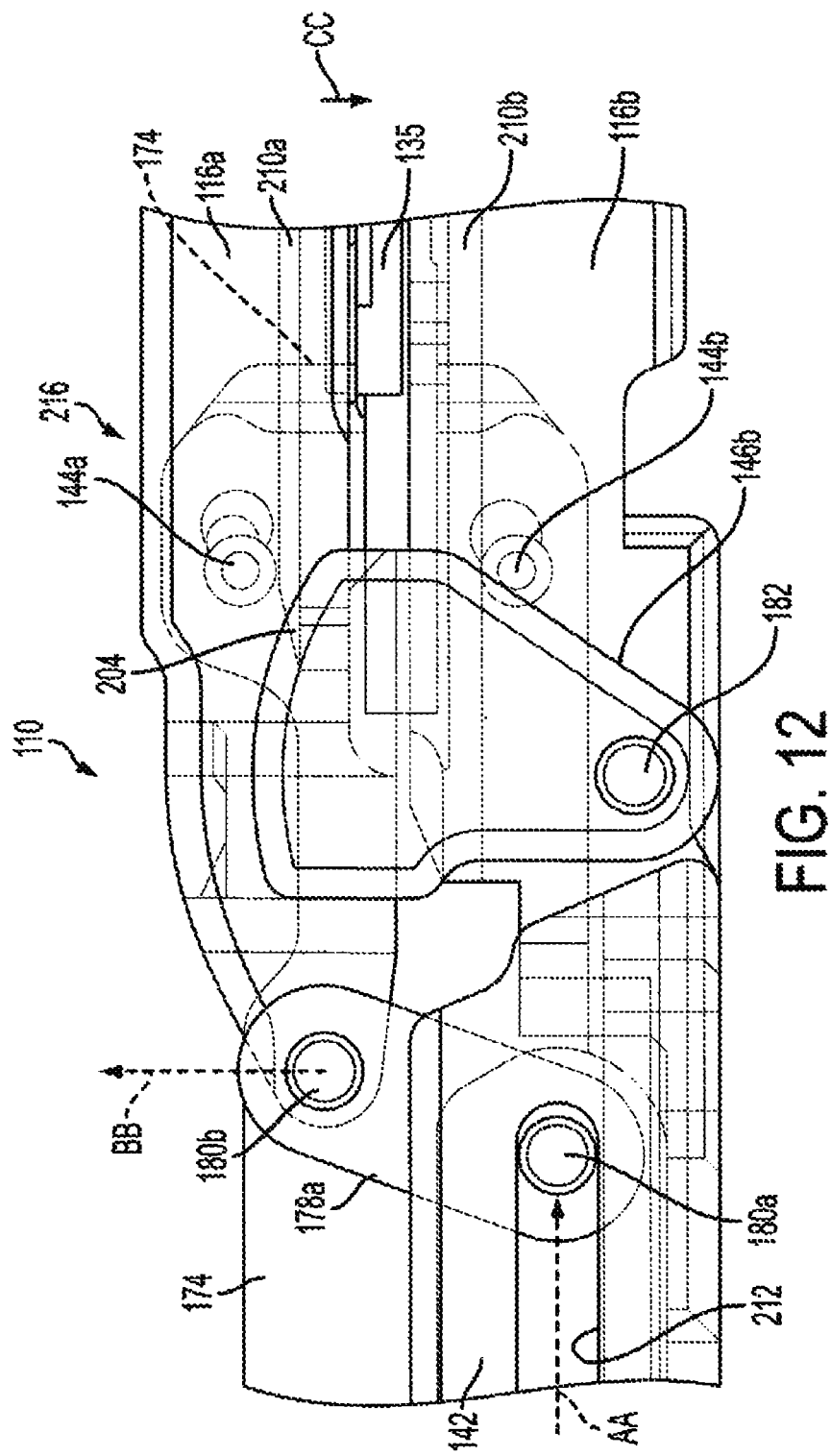
FIG. 12 shows the closure bar and I-beam member further advanced distally than shown in FIG. 11 where the I-beam member is located at the top of the ramp in the upper jaw, according to one embodiment.

FIG. 12 shows the closure bar 142 and the I-beam member 216 further advanced distally in direction AA than shown in FIG. 11 where the I-beam member 216 is located at the top of the ramp 204 in the upper jaw 116a, according to one embodiment. In FIG. 12, the closure bar 142 is advanced further distally in direction AA in response to the closure actuator 129 acting on the closure spring 114 and continues pushing on the bottom pin 180a causing it to move further distally in direction AA within the slot 212. In response, the pivoting link 178a moves distally in direction AA and continues rotating counterclockwise pushing the top pin 180b upwardly in direction BB to apply a closing force to the upper jaw 116a. The upper jaw 116a continues rotating further in direction CC toward a closed position. At this stage, the I-beam member 216 is located at the top of the ramp 204.

Figure 13:
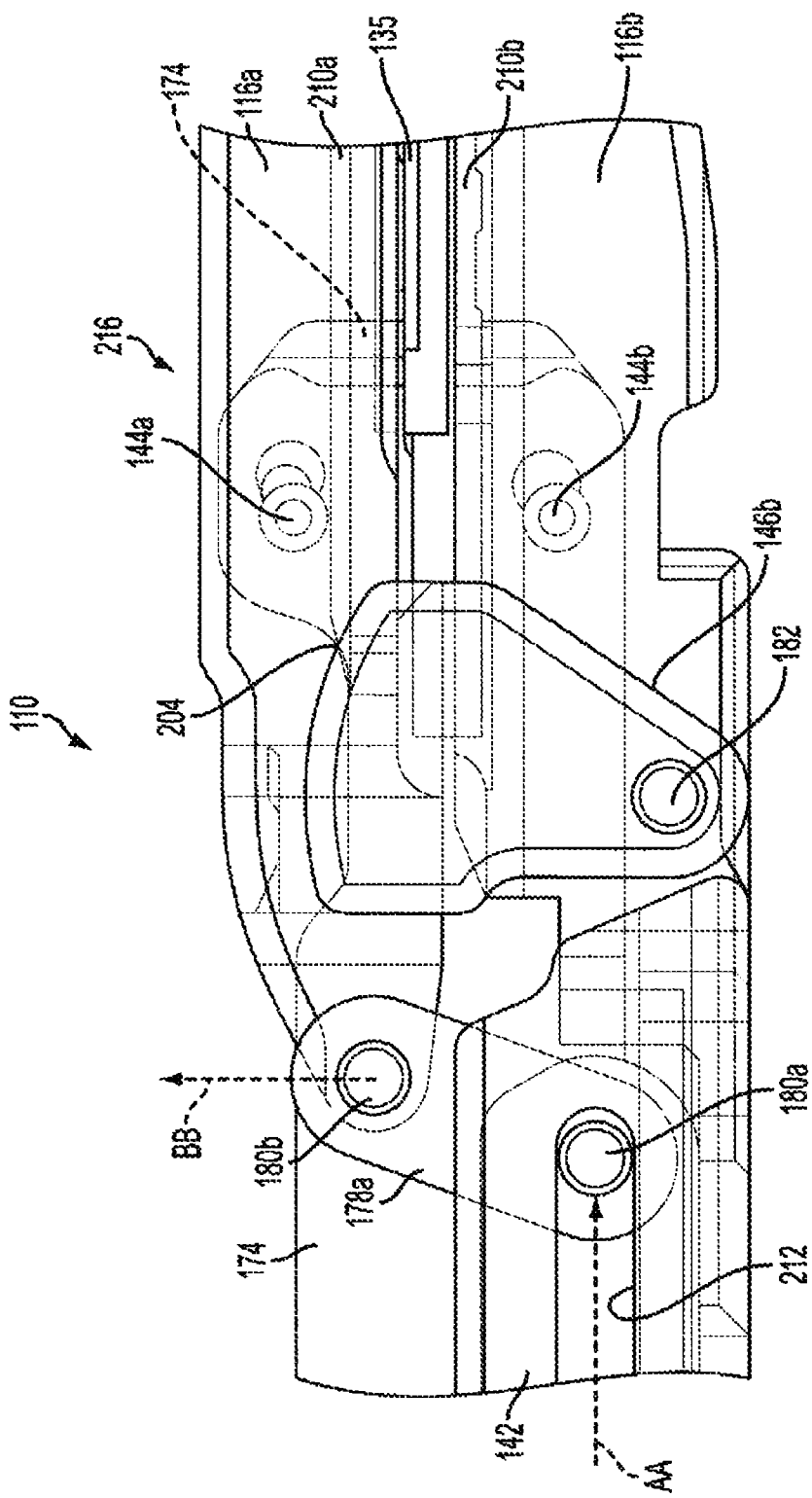
FIG. 13 shows the closure bar and I-beam member further advanced distally than shown in FIG. 12, where the I-beam member is located past the ramp in the upper jaw, according to one embodiment.

FIG. 13 shows the closure bar 142 and I-beam member 216 further advanced distally than shown in FIG. 12, where the I-beam member 216 is located past the ramp 204 in the upper jaw 116a, according to one embodiment. FIG. 13 shows the closure bar 142 advanced still further distally in direction AA and continues to push on the bottom pin 180a causing it to move distally in direction AA within the slot 212. In response, the pivoting link 178a moves distally in direction AA and continues rotating counterclockwise pushing the top pin 180b upwardly in direction BB to apply a closing force to the upper jaw 116a. The upper jaw 116a continues rotating further in direction CC toward a closed position. In FIG. 13, the I-beam member 216 is located past the ramp 204 and the upper jaw 116a is fully closed in response to the trigger plate 124 acting on the toggle clamp 145, which acts on the yoke 132, and advances the closure actuator 129 and the closure bar 142 to push on the pivoting link 178a. The I-beam member 216 pins 144a, 144b are now located past the ramp 204 and are located in the tracks 210a, 210b formed in the respective upper and lower jaws 116a, 116b. The I-beam member 216 is now prepared to slide distally in direction AA. In response to the trigger 109 being squeezed, the firing plate 128 rotates to advance the rack 136 distally, which acts on the firing bar 117 and pushes the I-beam member 216 and the cutting element 174 distally in direction AA. This action forces the jaws 116a, 116b fully shut to compress the tissue located therebetween.

With reference now to FIGS. 1-13, the disclosure now turns to a description of the electrosurgical instrument 102 having a separate spring driven cam closure mechanism for closing the jaws 110 that is independent of the I-beam 216 closure mechanism. In various embodiments, the present disclosure provides an electrosurgical radio frequency (RF) bipolar sealing device comprising a separate spring driven cam closure mechanism that is independent of the I-beam member 216 closure mechanism to simultaneously close a set of opposing jaws 116a, 116b. The spring driven cam closure system can close the jaws 116a, 116b first unless the force to close the jaws 116a, 116b overcomes a spring force. At this point, the I-beam member 216 closure system will close the jaws 116a, 116b. The spring driven cam closure mechanism comprises a spring 114 connected to a bar 142, which is in turn connected to a pivoting link 178a, which is then connected to a jaw 116a. Pushing on the spring 114 pushes on the bar 142, which pushes on the pivoting link 178a which closes the jaw 116a. The spring 114 of the cam closure system can be pre-compressed to raise its starting load.

The closure system of the electrosurgical instrument 102 comprises a first closure system comprising a spring driven cam closure mechanism and a second closure system comprising an I-beam closure mechanism. Both the first and second closure mechanisms are operated by the single trigger 109. The first closure system, otherwise referred to herein as a cam closure system, is driven by the closure of the trigger 109 in the first ~13 degrees of stroke. During the first stroke of the trigger 109, the trigger plate 124 drives the toggle clamp 145 and yoke 132 to advance the closure actuator 129 distally to compress the closure spring 114. The closure spring 114 drives the closure bar 142 which drives the pin 180a and the pivoting link 178a distally to close the upper jaw 116a independently of the I-beam closure mechanism. It should be noted that during the first stroke of the trigger 109, the rack 132 moves slightly distally to allow the driving bar 117 to push the I-beam member 216 from the base of the ramp 2014 to the top of the ramp 204. The second closure system is driven by the closure of the trigger in the last ~29 degrees of stroke. During the second stroke of the trigger 109, when the knife lockout mechanism is either unlocked or disabled, the firing plate 128 drives the first and second pinions 133, 134, which drives the rack 136 distally. The rack 136 is fixedly coupled to the firing bar 117, which drives the I-beam member 216 comprising the flexible cutting element 174.

The first closure system is configured to close the set of opposing jaws 116a, 116b in the end effector 110 using the closure spring 114 to drive the closure bar 142 to drive the pin 180a and the pivoting link 178a distally and close the upper jaw 116a onto the lower jaw 116b. The first closure system can apply more clamping force to the jaws 116a, 116b independently of the second closure system that employs the I-beam member 216 to close the jaws 116a, 116b. The additional closing force that is applied by the first closure system provides better grasping force between the jaws 116a, 116b than simply relying on the I-beam member 216 providing the initial closure force to the jaws 116a, 116b by moving the I-beam member 216 up to the top of the ramp 204.

To ensure that the I-beam member 206 will also be able to close the jaws 116a, 116b, the first and second closure systems operate in tandem. Thus, the cam closure drive system comprising the closure bar 142 and pivoting link 178a and I-beam drive system comprising the I-beam member 216 and firing bar 117 operate in tandem. In one embodiment, the cam closure system closes the jaws 116a, 116b and moves along with the I-beam member 216. Some conventional electrosurgical devices employ the toggle clamp 145 to move the I-beam member 216 to close the jaws 116a, 116b. In the present embodiment, however, the first closure system is operably coupled to the toggle clamp 145 in conjunction with the second closure system such that both closure systems advance distally at the same time. The cam closure system can be timed to close the jaws 116a, 116b before the I-beam member 216. The cam closure system also can incorporate an inline closure spring 114. The inline closure spring 114 can compress at the end of the closure stroke (after the first ~13 degrees of stroke of the trigger 109) to keep the jaws 116a, 116b shut with a set spring force.

When material is located between the jaws 116a, 116b, the closure spring 114 will be compressed over a predetermined limit during the first stroke closure phase of the cam closure system. After the predetermined limit, the I-beam member 216 closure system takes over the function of closing the jaws 116a, 116b. Accordingly, in the illustrated system the I-beam member 216 will ensure that the jaws 116a, 116b always fully close using jus the toggle clamp 145. The I-beam member 216 is configured to only close the jaws 116a, 116b when the material located between the jaws 116a, 116b takes more force to close than the cam closure spring 114 can provide. The cam system also provides a rising mechanical advantage as the upper jaw 116a is closed such that the more compression force is applied to the closure spring 114 the less force is exerted on the jaws 116a, 116b to prevent damaging tissue from too much spring force.

In one embodiment, the closure system comprising a first closure system (spring cam closure system) and a second an I-beam and spring driven cam system to simultaneously close a set of opposing jaws can be configured to operate in the following manner: (1) place tissue in the jaws and pull the trigger; (2) the toggle clamp pushes on the I-beam and the cam closure; (3) the cam immediately pushes on the jaw through a spring to close it, the I-beam trails a closure ramp on the upper jaw; (4) the cam fully closes the jaws before the toggle stops moving; (5) the toggle clamp continues to move (e.g., another 0.05 inches) to compress the closure spring to ensure the jaws are sprung closed, the I-beam moves over the top of the ramp; and (6) thick tissue in the jaws may compress the spring on the cam closure before the end of the toggle stroke, the I-beam will hit the closure ramp and force the jaws closed to ensure that the I-beam will repeatedly be located over the ramp with the jaws closed before the toggle stops moving.

The disclosed closure system comprising a first spring driven cam closure system and a second I-beam driven closure system is configured to simultaneously close a set of opposing jaws 116a, 116b and provides several advantages over conventional devices. The disclosed device is capable of sealing tissue without necessarily cutting the tissue, provides improved tissue grasping without actuating the cutting element 174, locates the I-beam member 216 over the ramp 204 before the I-beam 216 gear train takes over to provide lower force to fire the cutting element 174. The disclosed closure system also provides improved jaw 116a opening and tissue dissection over conventional devices. The disclosed closure system also provides lower force to fire from preload on tissue. The gears coupled to the firing plate 128 fire the I-beam member 216 distally and can be configured to operate with conventional electrosurgical jaw designs. Additional advantages, not necessarily described herein, are also provided.

Figure 14:
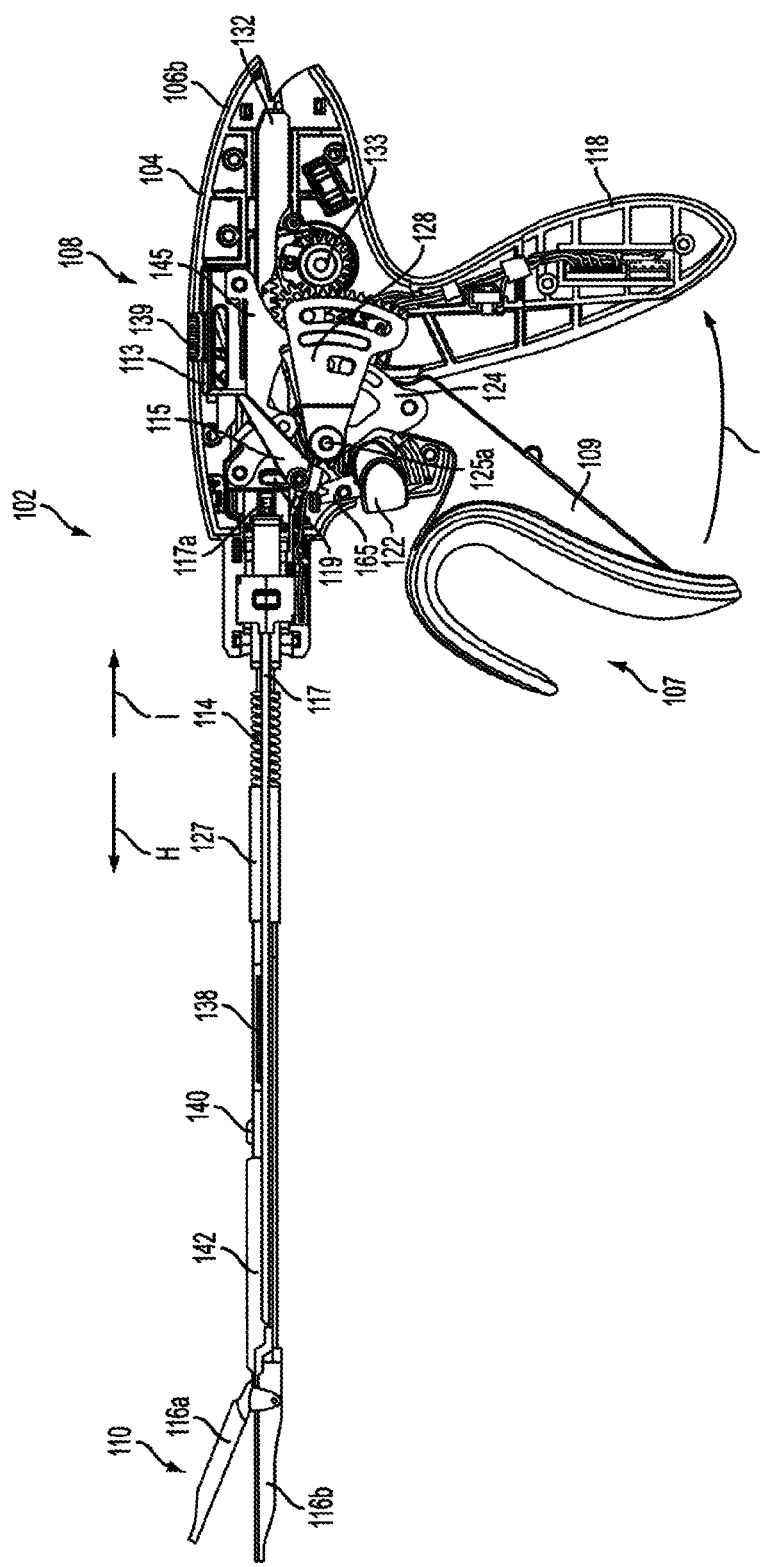
FIG. 14 is a side elevational view of the surgical instrument shown in FIGS. 1 and 2 with the left housing shroud removed, shaft assembly sheaths removed, and the jaw fully open, according to one embodiment.

FIGS. 14-23 provide a general description of the surgical instrument 102 shown in FIGS. 1 and 2 comprising a first spring driven cam closure system that operates independently of a second I-beam driven closure system. FIGS. 14-23 illustrate the surgical instrument 102 shown in FIGS. 1 and 2 with the jaw 110 fully open and the lockout defeat mechanism 108 enabled, e.g., in the "ON" position. FIG. 14 is a side elevational view of the surgical instrument 102 shown in FIGS. 1 and 2 with the left housing 106a shroud removed, shaft assembly 112 sheaths removed, the jaw 110 fully open and the lockout defeat mechanism 108 enabled, e.g., in the "ON" position, according to one embodiment. Thus, the button 139 portion of the slider 113 is slidably moved proximally to locate it in the B position.

Figure 15:
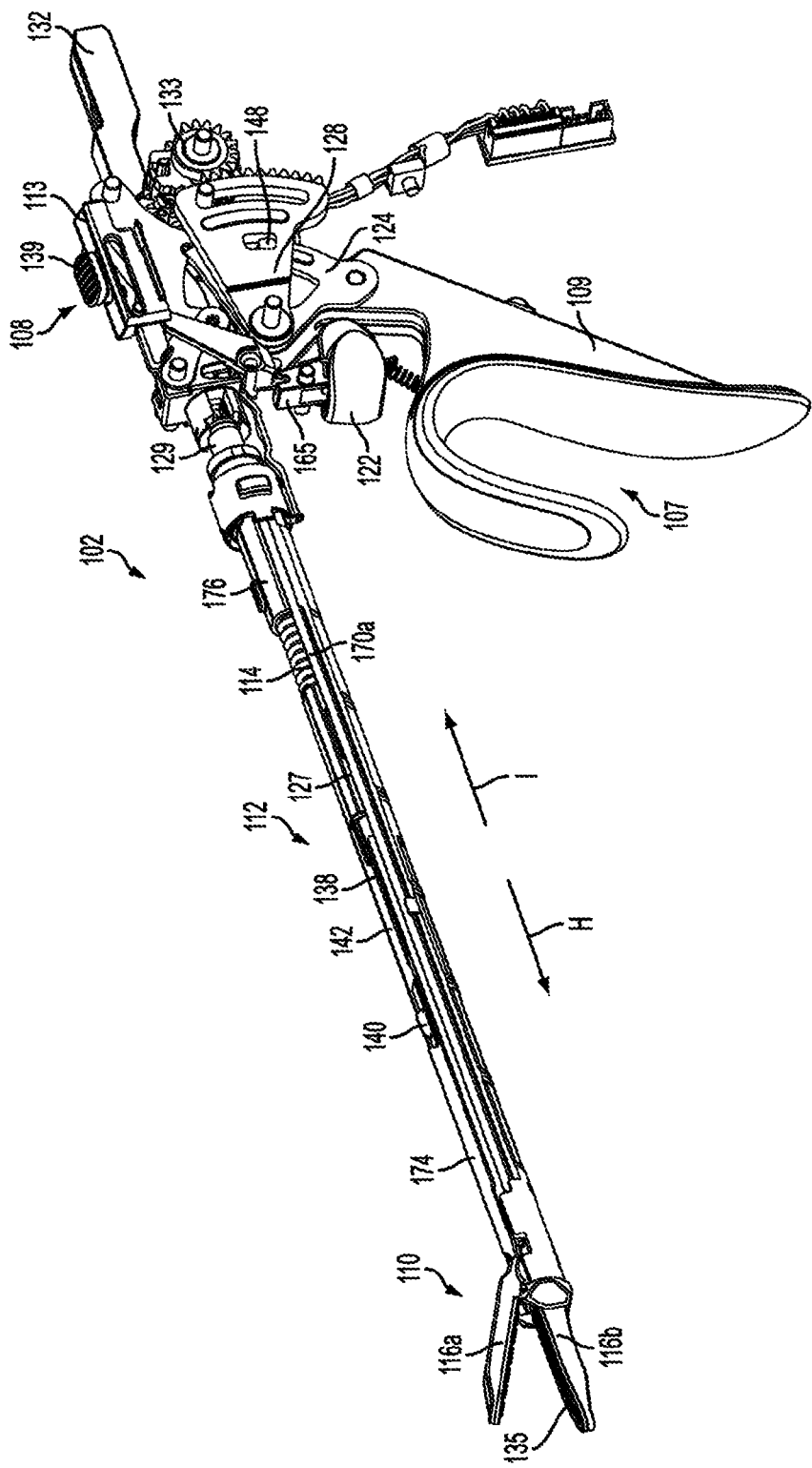
FIG. 15 is a perspective view of the surgical instrument shown in FIG. 14 with the right housing shroud removed, according to one embodiment.
Figure 16:
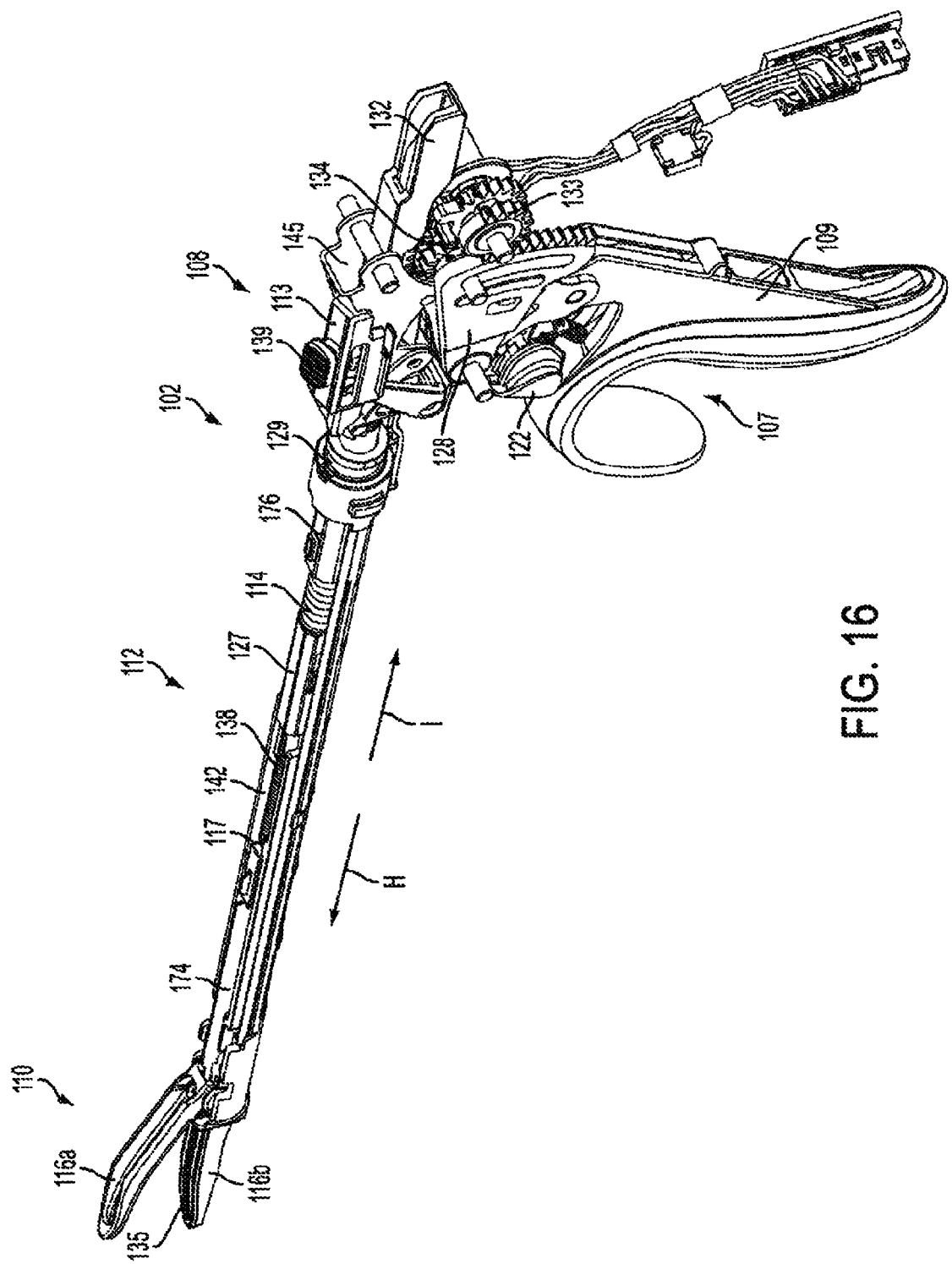
FIG. 16 is another perspective view of the surgical instrument shown in FIG. 15, according to one embodiment.

FIG. 15 is a perspective view of the surgical instrument 102 shown in FIG. 14 with the right housing shroud 106b removed, according to one embodiment. FIG. 16 is a perspective view of the surgical instrument 102 shown in FIG. 15, according to one embodiment.

Figure 17:
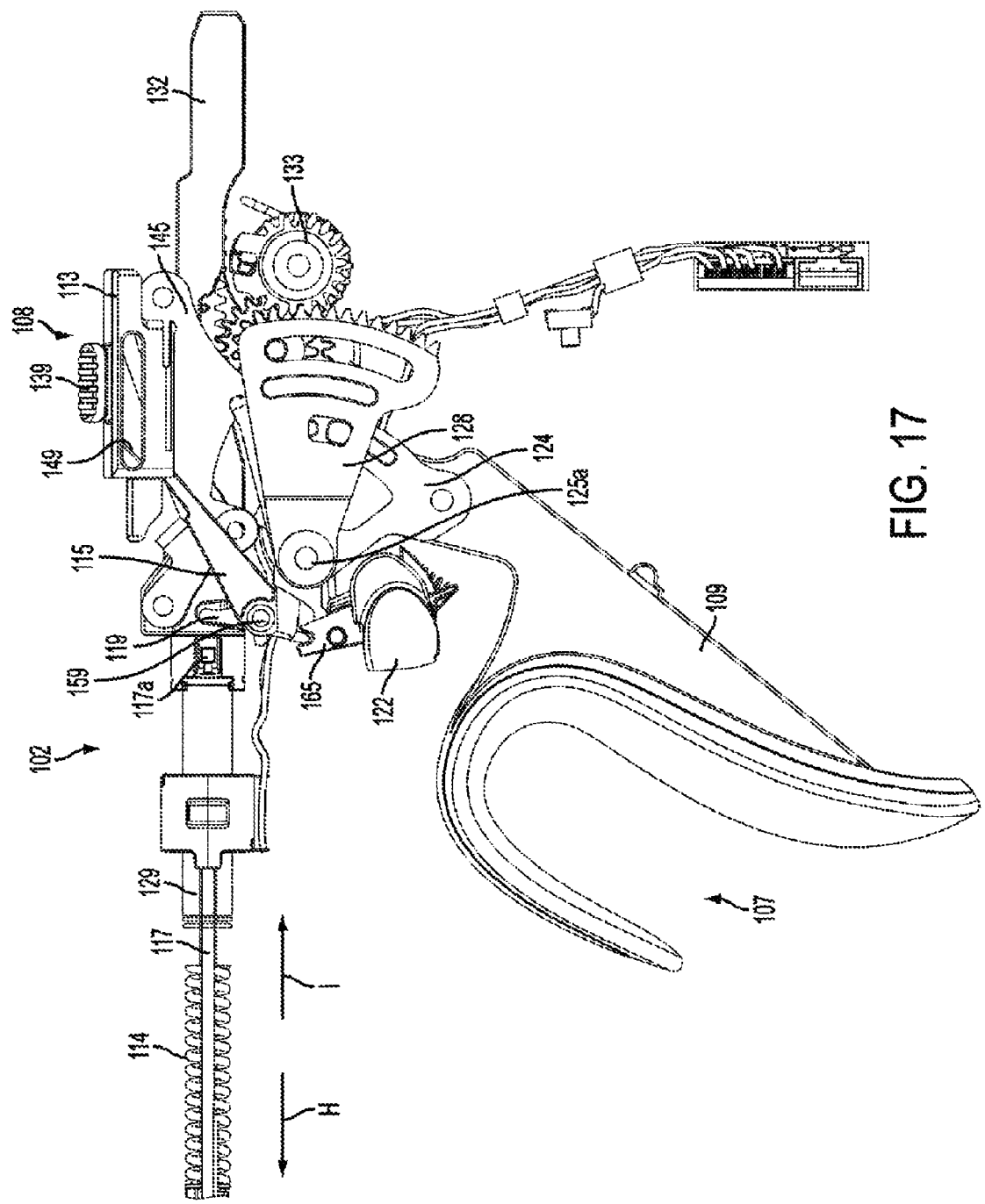
FIG. 17 is a side elevational view of the surgical instrument shown in FIG. 14 with the right housing shroud removed, according to one embodiment.

FIG. 17 is a side elevational view of the surgical instrument 102 shown in FIG. 14 with the right housing shroud 106b removed, according to one embodiment. The trigger 109 is located in the maximum distal position and the trigger plate 124 is engaged with the toggle clamp 145 and yoke 132, which are located in the maximum proximal position to set the jaws 110 in the fully open position. The slider 113 is set to the maximum proximal "B" position where the angled wall (ramp) 149 has rotated the lever arm 115. The lever arm 115 rotates the unlock arm 119 clockwise and the lockout element 165 counterclockwise to enable the lockout defeat mechanism 108. The lockout element 165 also depresses the energy button 122 to indicate that the lockout defeat mechanism 108 enabled in the "ON" position. This view also shows the position of the firing plate 128 sector gear meshed with the first pinion 133 prior to firing the cutting element. In this configuration the jaws 116a, 116b can be fully closed independently of the firing bar 117 driving the I-beam member 216 by squeezing the trigger 109 to drive the toggle clamp 145 and the closure spring 114.

Figure 18:
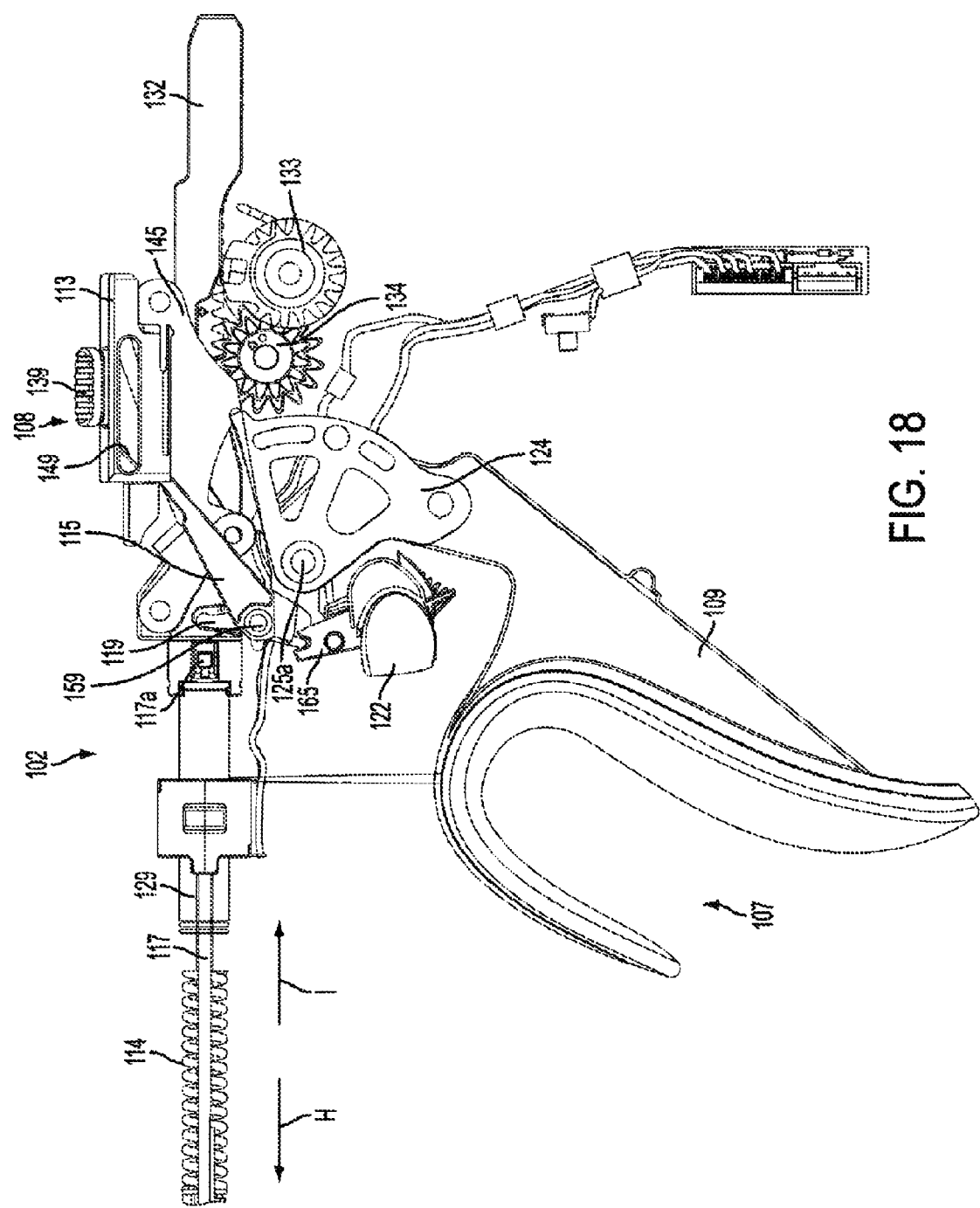
FIG. 18 is a side elevational view of the surgical instrument shown in FIG. 14 with the firing plate removed, according to one embodiment.

FIG. 18 is a side elevational view of the surgical instrument shown in FIG. 17 with the firing plate 128 removed, according to one embodiment. This view illustrates the position of the trigger 109 relative to the trigger plate 124, the toggle clamp 145, and the yoke 132. This view also shows the first pinion 133 meshed with the second pinion 134 which located behind the firing plate 128.

Figure 19:
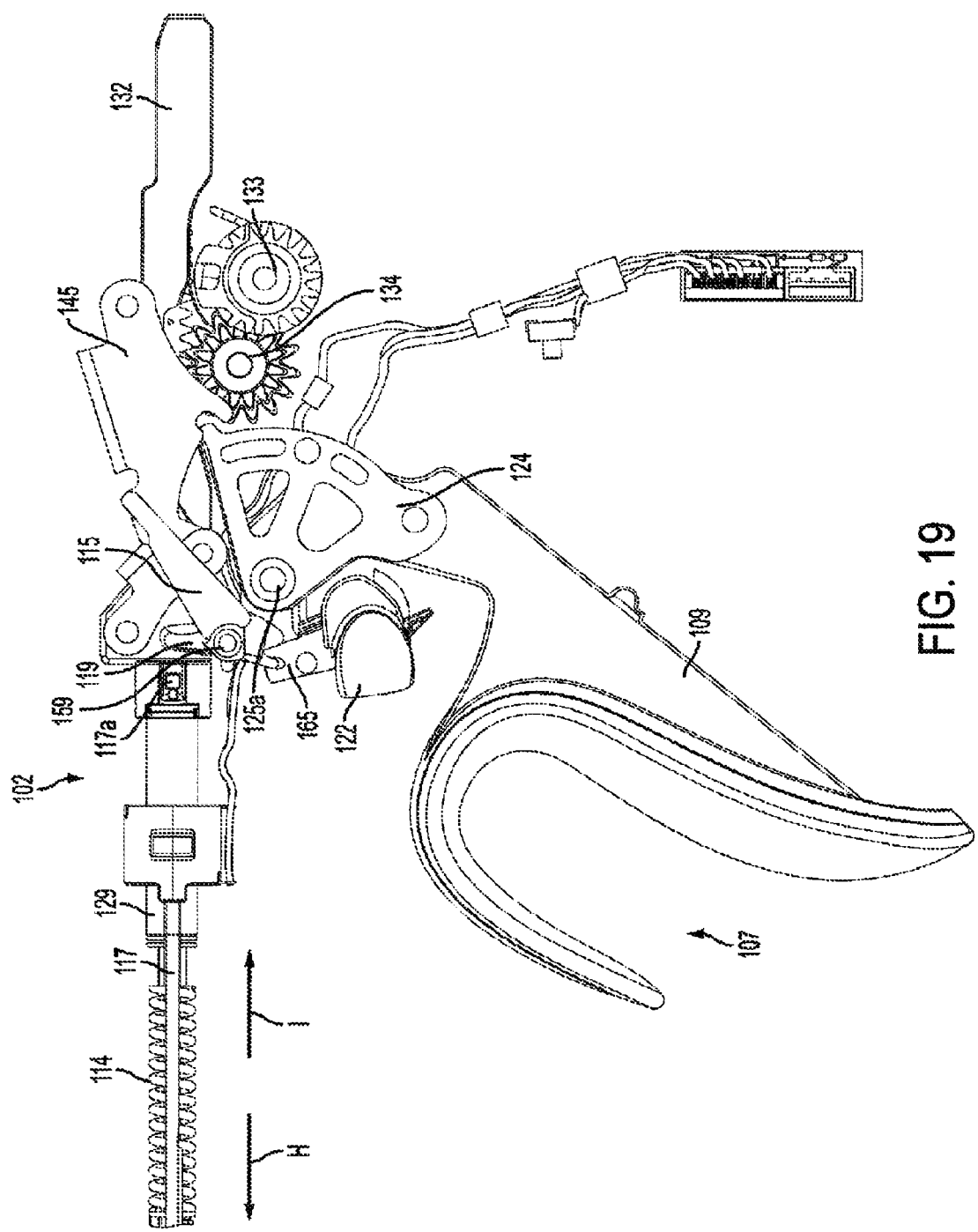
FIG. 19 is a side elevational view of the surgical instrument shown in FIG. 18 with the lockout defeat mechanism slider removed, according to one embodiment.

FIG. 19 is a side elevational view of the surgical instrument 102 shown in FIG. 18 with the lockout defeat mechanism slider 113 removed, according to one embodiment, to better illustrate the position of the toggle clamp 145 when the jaws 110 are fully open.

Figure 20:
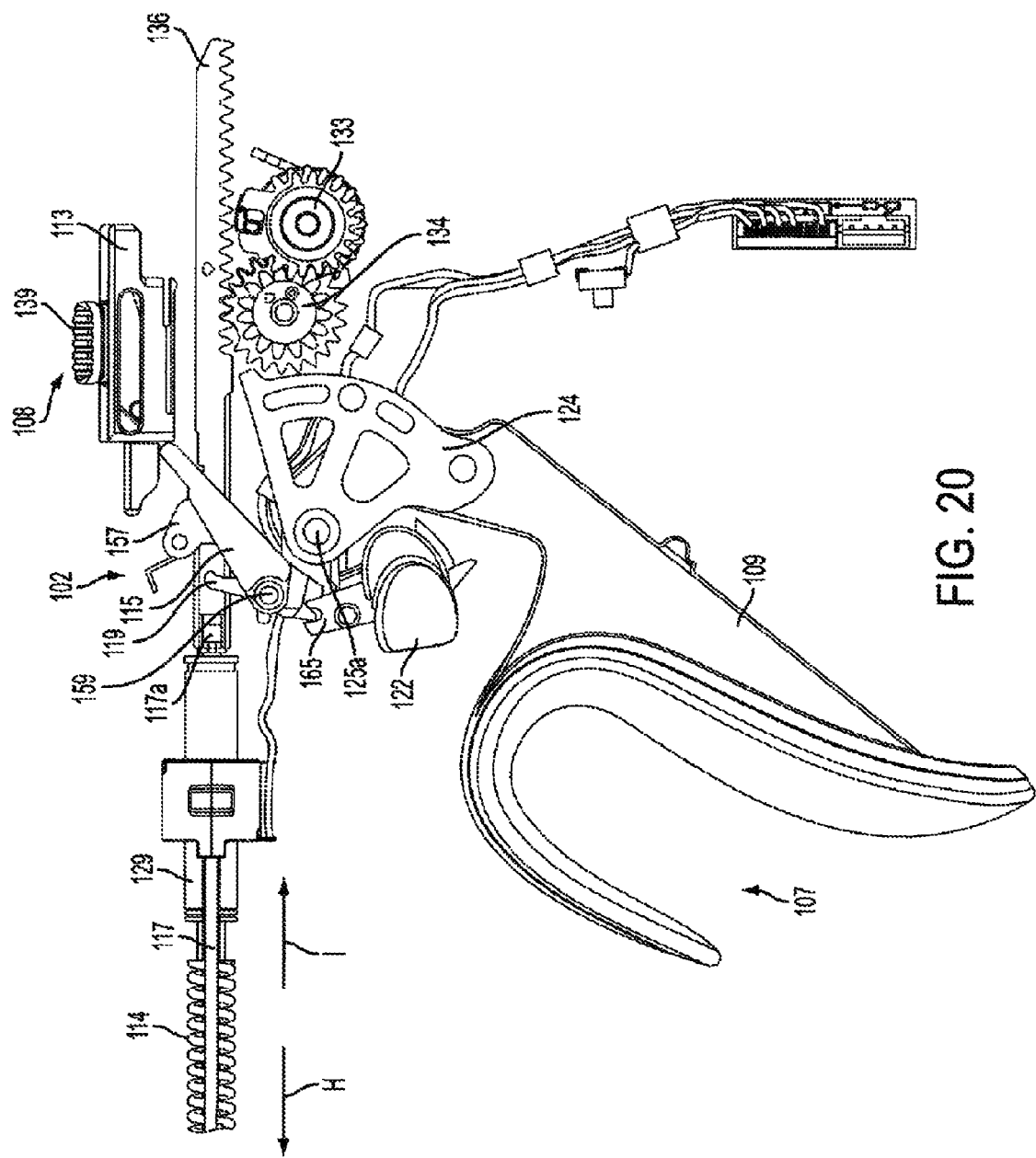
FIG. 20 is a side elevational view of the surgical instrument shown in FIG. 18 with the toggle clamp and yoke removed, according to one embodiment.

FIG. 20 is a side elevational view of the surgical instrument 102 shown in FIG. 19 with the toggle clamp 145 and the yoke 132 removed, according to one embodiment. This view shows the position of the rack 136 and the lock arm 157 relative to the position of the slider 113. In addition, this view shows the second pinion 134 meshed with the rack 136 when the cutting element has not yet been fired.

Figure 21:
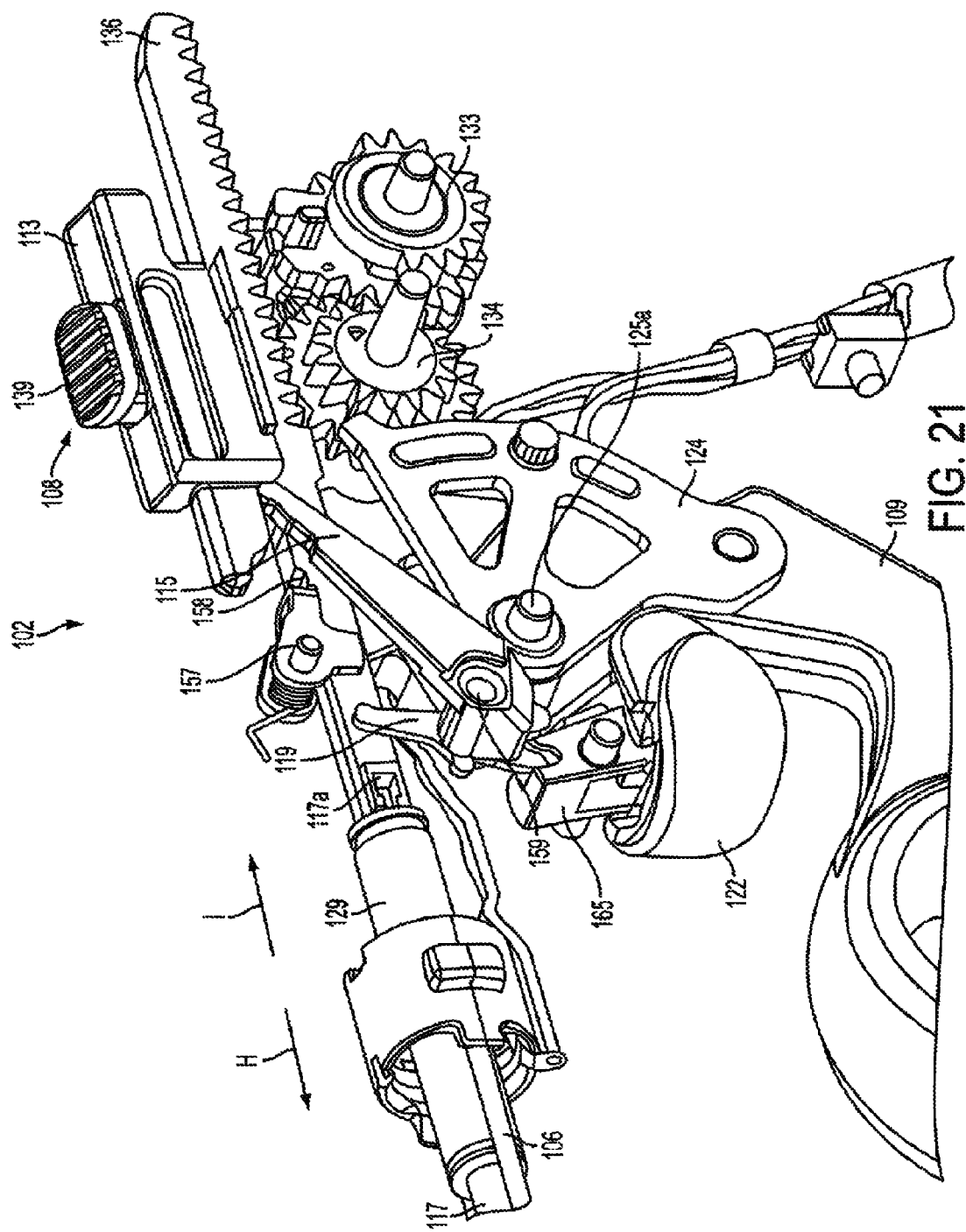
FIG. 21 is a partial perspective view of the surgical instrument shown in FIG. 20, according to one embodiment.

FIG. 21 is a partial perspective view of the surgical instrument 102 shown in FIG. 20, according to one embodiment, which more clearly shows the lock arm 157 located in the notch 158 formed on top of the rack 136. When the unlock arm 119 is in the indicated position, as the toggle clamp 145 and yoke move in the distal direction, the unlock arm 119 acts on the lock arm 157 to disengage the lock arm 157 from the notch 158 in the rack 136 to defeat the lockout mechanism. Therefore, the rack 136 is able to advance distally when the firing plate 128 is rotated by the trigger 109.

Figure 22:
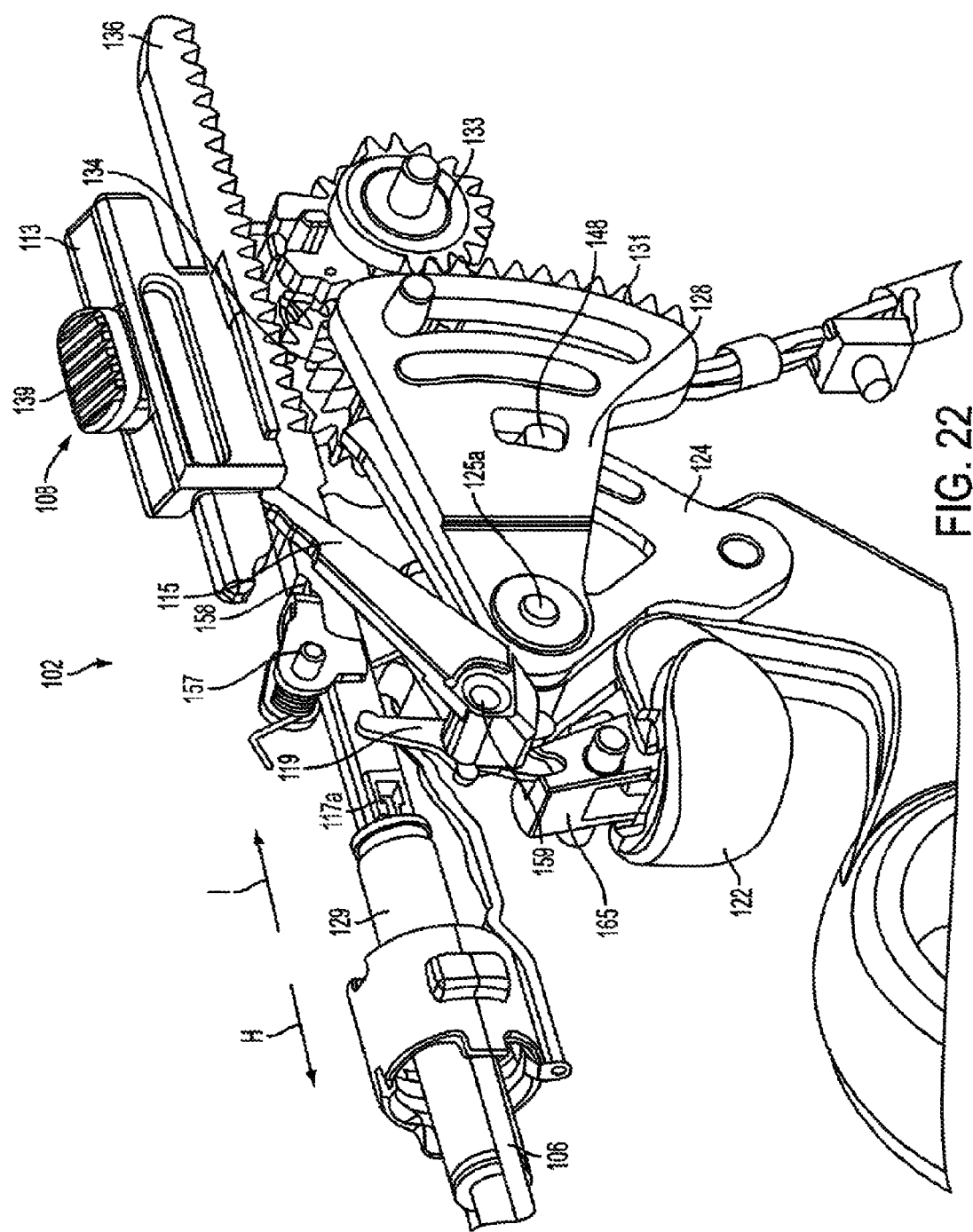
FIG. 22 is a partial perspective view of the surgical instrument shown in FIG. 21 with the firing plate replaced, according to one embodiment.

FIG. 22 is a partial perspective view of the surgical instrument shown in FIG. 21 with the firing plate 128 replaced, according to one embodiment, to show the relative position of the firing plate 128, the first and second pinions 133, 134 and the rack 136 prior to firing the cutting element.

Figure 23:
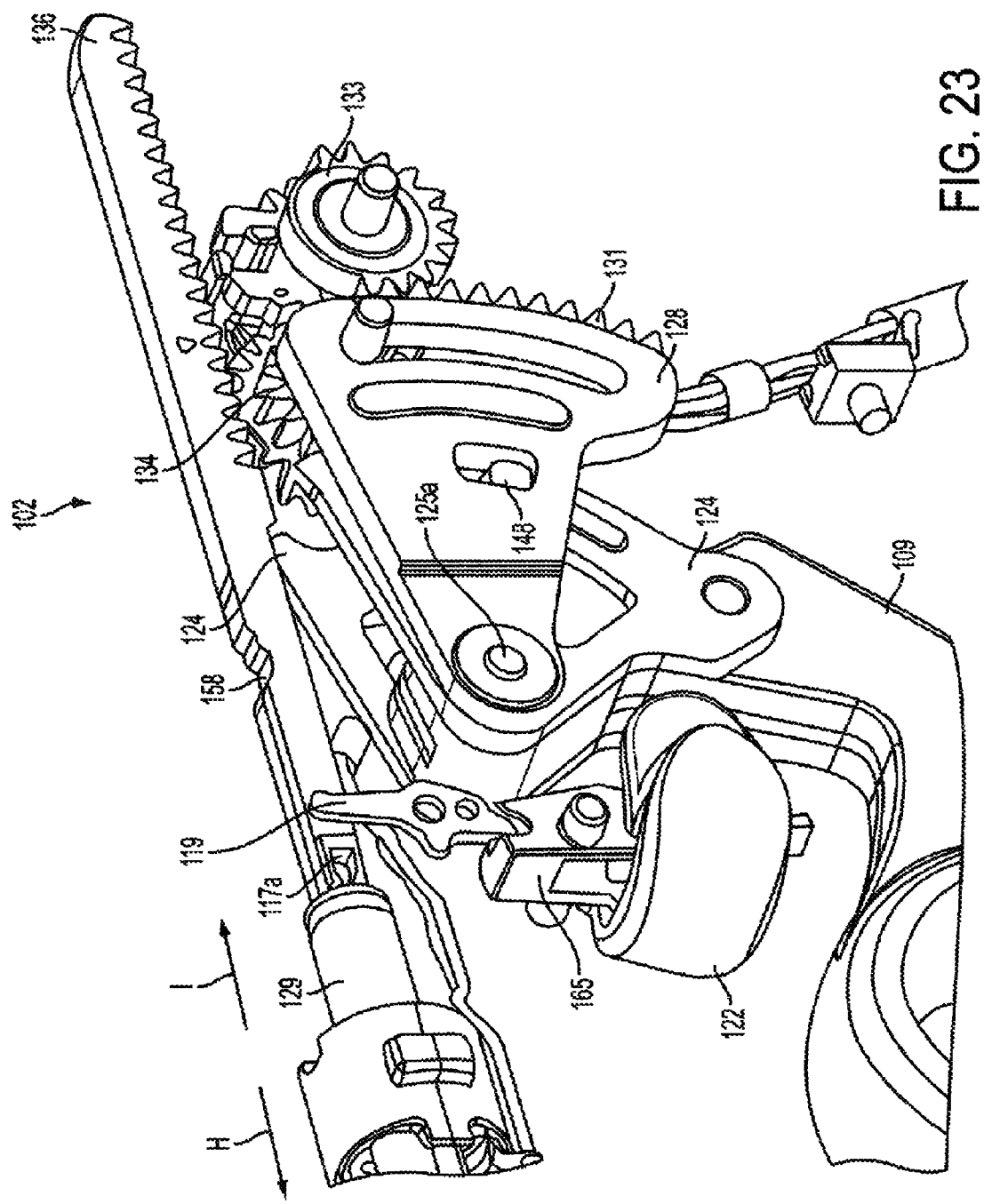
FIG. 23 is a partial perspective view of the surgical instrument shown in FIG. 22 with the lockout defeat mechanism slider, lever arm, and lock arm removed, according to one embodiment.

FIG. 23 is a partial perspective view of the surgical instrument 102 shown in FIG. 22 with the lockout defeat mechanism slider 113, lever arm 115, and lock arm 157 removed, according to one embodiment, to show the notch 158 or slot formed on top of the rack 136. As previously discussed, the lock arm 157 engages the notch 158 to prevent the rack 136 from advancing distally to fire the cutting element in response to the squeezing the trigger 109.

Figure 24:
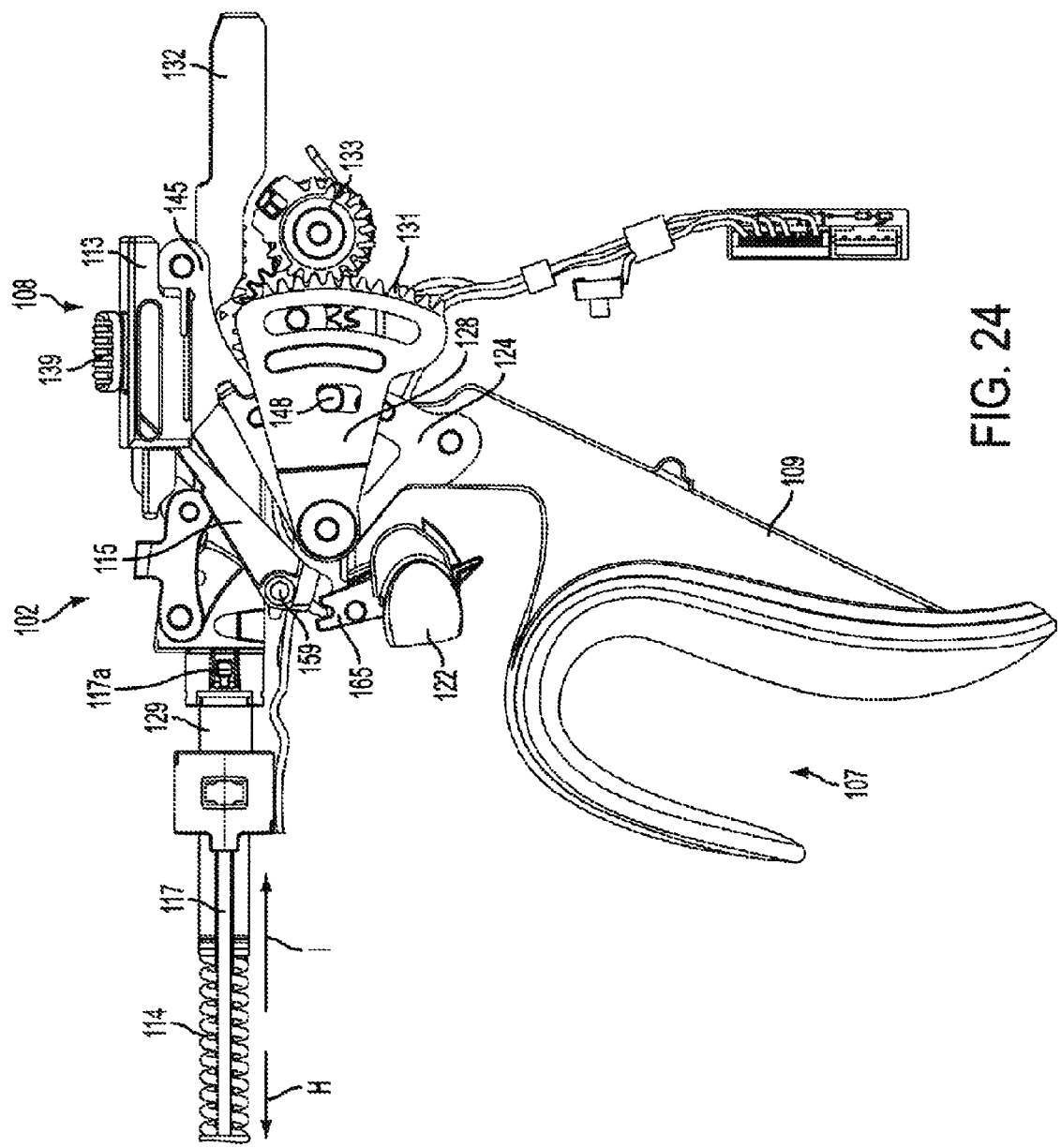
FIG. 24 is a side elevational view of the surgical instrument shown in FIGS. 1 and 2 with the left and right housing shrouds removed, shaft assembly sheaths removed, jaws clamped, and the lockout defeat mechanism enabled, e.g., in the "ON" position, according to one embodiment.

FIG. 24 is a side elevational view of the surgical instrument 102 shown in FIGS. 1 and 2 with the left and right housing shrouds 106a, 106b removed, shaft assembly 112 sheaths removed, the jaws 116a, 116b clamped and the lockout defeat mechanism 108 enabled, e.g., in the "ON" position, according to one embodiment. The trigger plate 124 is fully rotated counterclockwise to straighten the toggle clamp 145 and drive the yoke 132 distally in direction H. To fully close the jaw 110, the trigger 109 is squeezed in direction C to rotate the trigger plate 124 fully counterclockwise to straighten the toggle clamp 145 and advanced the yoke 132. Since the knife 174 has not been fired, the trigger 109 has not been fully squeezed and the firing plate 128 has not been rotated to actuate the rack 136. The yoke 132 is coupled to the closure actuator 129 which compresses the closure spring 114 and drives the closure bar 142. The closure bar 142 is coupled to the pivoting link 178a which closes the upper jaw 116a.

Figure 25:
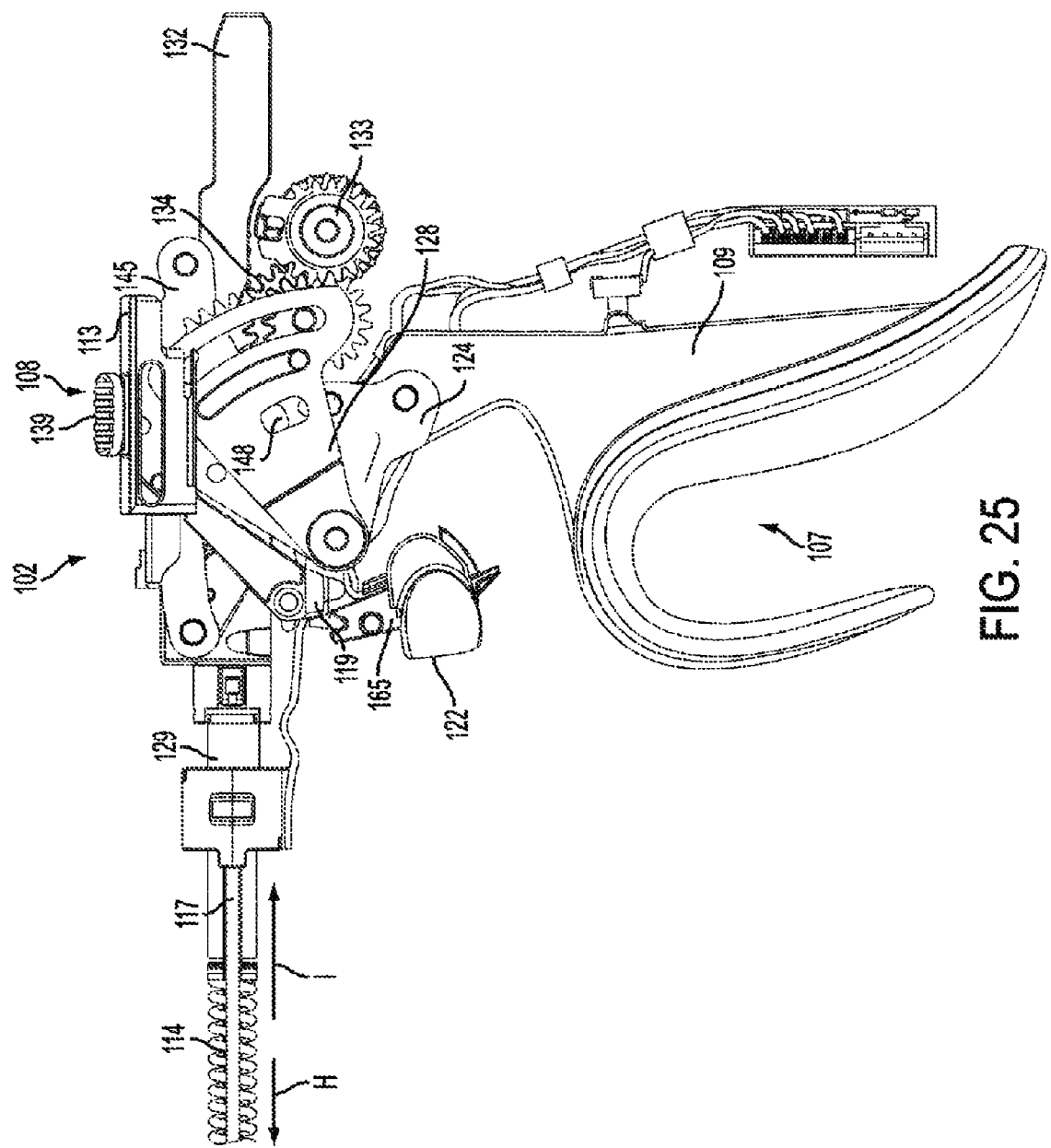
FIG. 25 is a side elevational view of the surgical instrument shown in FIGS. 1 and 2 with the left and right housing shrouds removed, shaft assembly sheaths removed, jaws fully closed, knife fully fired, and the lockout defeat mechanism disabled, e.g., in the "OFF" position, according to one embodiment.

FIG. 25 is a side elevational view of the surgical instrument 102 shown in FIGS. 1 and 2 with the left and right housing shrouds 106a, 106b removed, shaft assembly 112 sheaths removed, jaws 116a, 116b fully closed, knife 174 fully fired, and the lockout defeat mechanism 108 disabled, e.g., in the "OFF" position, according to one embodiment. The button 139 portion of the slider 113 is slidably moved distally to locate it in the A position. To fully close the jaw 110, the trigger 109 is squeezed in direction C to rotate the trigger plate 124 fully counterclockwise to straighten the toggle clamp 145 and advanced the yoke 132. As indicated by the position of the trigger 109 and the firing plate 128, the knife 174 is fully fired.

Figure 26:
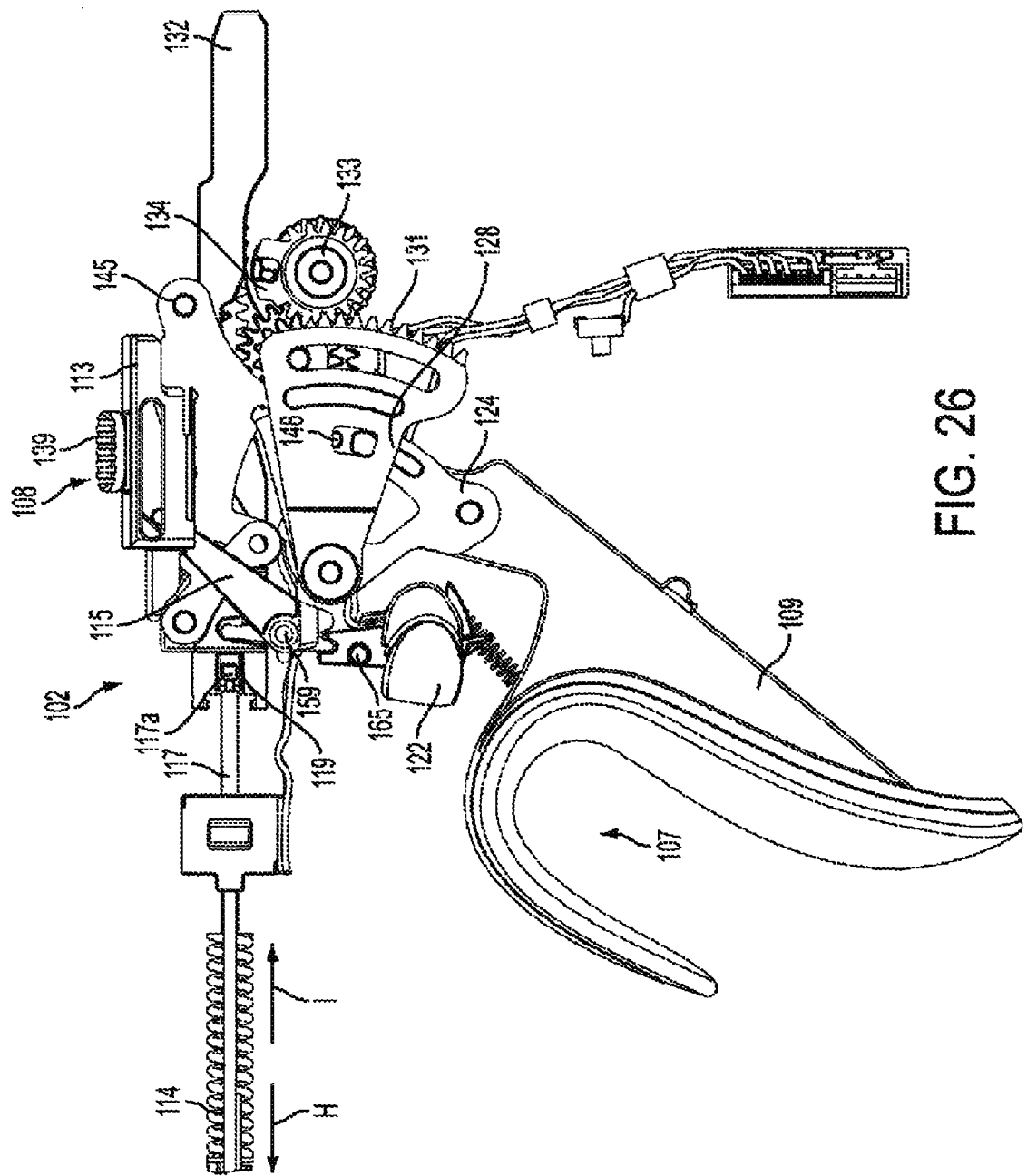
FIG. 26 is a side elevational view of the surgical instrument shown in FIGS. 1 and 2 with the left and right housing shrouds removed, shaft assembly sheaths removed, jaws fully open, knife not fired, and the lockout defeat mechanism disabled, e.g., in the "OFF" position, according to one embodiment.

FIG. 26 is a side elevational view of the surgical instrument 102 shown in FIGS. 1 and 2 with the left and right housing shrouds 106a, 106b removed, shaft assembly 112 sheaths removed, jaws 116a,116b fully open, knife 174 not fired, and the lockout defeat mechanism disabled 108, e.g., in the "OFF" position, according to one embodiment. To fully fire the knife while the lockout defeat mechanism 108 disabled, e.g., in the "OFF" position (in other words, the lockout mechanism is enabled) the energy button 122 must be depressed to rotate the lockout element 165 counterclockwise and rotate the unlock arm 119 clockwise to kick the lock arm 157 out of the notch 158 in the rack 136 and unlock the lockout mechanism. Once the lockout mechanism in unlocked, the trigger 109 can be fully squeezed in direction C to rotate the firing plate 128 counterclockwise. This rotates the first pinion 133 clockwise, the second pinion 134 counterclockwise, and the rack 136 is driven distally to fire the firing bar 117 distally in direction H to fire the knife 174 and the I-beam member 216.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

The invention claimed is:

1. A surgical instrument, comprising:
   an end effector comprising:
      a movable jaw comprising a first jaw member and a second jaw member, the first jaw member comprising a first track configured to slidably receive a first pin, the first jaw member comprising a ramp at a proximal end of the first track, the second jaw member comprising a second track configured to slidably receive a second pin; and
      a cutting element slidably movable within the end effector, wherein the first and second pins are fixed to the cutting element, wherein the cutting element and the first and second pins define an I-beam member; and
   a handle assembly comprising:
      an energy button configured to deliver energy to at least one electrode located in the end effector;
      a trigger plate operably coupled to a spring, the spring configured to move the first jaw member a first predetermined distance relative to the second jaw member independently of the I-beam member based on the spring generating a predetermined force;
      a firing plate operably coupled to the I-beam member, the firing plate configured to drive the I-beam member based on a firing bar independently of the spring, wherein the I-beam member is configured to move the first jaw member relative to the second jaw member a second predetermined distance based on moving the I-beam member along the ramp and the first and second tracks from an initial position at a base of the ramp; and
      a trigger operatively coupled to the trigger plate and the firing plate; and
   wherein:
      the spring and the I-beam member are configured to simultaneously move the first jaw member relative to the second jaw member, and
      the predetermined force is less than a predetermined threshold.

2. The surgical instrument of claim 1, wherein the spring is further configured to provide a rising mechanical advantage.

3. The surgical instrument of claim 2, wherein the spring is pre-compressed to increase a starting load.

4. The surgical instrument of claim 2, further comprising:
   a motion bar coupled to the spring; and a pivoting link having a proximal end and a distal end, the proximal end coupled to the motion bar and the distal end coupled to the movable jaw.

5. The surgical instrument of claim 4, further comprising a closure actuator coupled to the spring and coupled to the trigger plate via a toggle clamp, wherein the closure actuator is configured to compress the spring.

6. The surgical instrument of claim 1, further comprising:
the firing bar having a proximal end and a distal end, wherein the cutting element is coupled to the distal end of the firing bar; and
a rack coupled to the proximal end of the firing bar, wherein the rack is operatively coupled to the firing plate.

7. The surgical instrument of claim 1, further comprising a lockout disabling mechanism comprising a lock arm operatively coupled to a lever arm and a lockout element, wherein the lockout element is configured to prevent driving the cutting element.

8. A surgical instrument, comprising:
an end effector comprising:
a movable jaw comprising a first jaw member and a second jaw member, the first jaw member comprising a first track configured to slidably receive a first pin, the first jaw member comprising a ramp at a proximal end of the first track, the second jaw member comprising a second track configured to slidably receive a second pin; and
a cutting element slidably movable within the end effector, wherein the first and second pins are fixed to the cutting element, wherein the cutting element and the first and second pins define an I-beam member; and
a spring configured to move the first jaw member a first predetermined distance relative to the second jaw member independently of the I-beam member; and
wherein:
the I-beam member is configured to independently move the first jaw member a second predetermined distance relative to the second jaw member based on moving the I-beam member along the ramp and the first and second tracks from an initial position at a base of the ramp,
the spring and the I-beam member are configured to simultaneously move the first jaw member relative to the second jaw member,
the first predetermined distance is less than a predetermined threshold distance.

9. The surgical instrument of claim 8, wherein the spring is pre-compressed to increase a starting load.

10. The surgical instrument of claim 8, further comprising:
a motion bar coupled to the spring; and
a pivoting link having a proximal end and a distal end, the proximal end coupled to the motion bar and the distal end coupled to the movable jaw.

11. The surgical instrument of claim 8, further comprising a closure actuator having a proximal end and a distal end, the distal end coupled to the spring and the proximal end coupled to a toggle clamp configured to drive the closure actuator, wherein the closure actuator is configured to compress the spring when the closure actuator moves in a distal direction.

12. The surgical instrument of claim 8, further comprising:
a firing bar having a proximal end and a distal end, wherein the cutting element is coupled to the distal end of the firing bar; and
a rack coupled to the proximal end of the firing bar, wherein the rack is operatively coupled to a firing plate.

13. The surgical instrument of claim 8, further comprising a lockout disabling mechanism comprising a lock arm operatively coupled to a lever arm and a lockout element, wherein the lockout element is configured to prevent driving the cutting element.

14. A surgical instrument, comprising:
a handle assembly comprising:
a trigger operatively coupled to a trigger plate and a firing plate;
an energy button configured to deliver energy to at least one electrode;
a lockout element operatively coupled to the energy button, the lockout element configured to prevent operation of the firing plate; and
a lockout disabling mechanism configured to disable the lockout element, the lockout disabling mechanism operable between a first position and a second position, wherein when the lockout disabling mechanism is located in the first position, the lockout element is enabled and can be unlocked by the energy button, and wherein when the lockout disabling mechanism is in the second position, the lockout element is disabled;
a shaft assembly comprising a proximal end and a distal end, wherein the shaft assembly is coupled to the handle assembly at the proximal end; and
an end effector coupled to the distal end of the shaft assembly, the end effector comprising:
a jaw assembly, comprising:
a first jaw member, the first jaw member comprising a first track configured to slidably receive a first pin, the first jaw member comprising a ramp at a proximal end of the first track; and
a second jaw member, the second jaw member comprising a second track configured to slidably receive a second pin, wherein rotation of the trigger plate transitions the jaw assembly between an open configuration and an approximated configuration by moving at least one of the first jaw member and the second jaw member relative to the other one of the first jaw member and the second jaw member;
a cutting element deployable in response to rotation of the firing plate wherein the first and second pins are fixed to the cutting element, wherein the cutting element and the first and second pins define an I-beam member;
a spring configured to move the first jaw member a first predetermined distance relative to the second jaw member independently of the I-beam member; and
wherein:
the I-beam member is configured to independently move the first jaw member a second predetermined distance relative to the second jaw member based on moving the I-beam member along the ramp and the first and second tracks from an initial position at a base of the ramp,
the spring and the I-beam member are configured to simultaneously move the first jaw member relative to the second jaw member; and
the first predetermined distance is less than a predetermined threshold distance.

15. The surgical instrument of claim 14, wherein the spring is pre-compressed to increase a starting load.

16. The surgical instrument of claim 14, further comprising:
   a motion bar coupled to the spring; and
   a pivoting link having a proximal end and a distal end, the proximal end coupled to the motion bar and the distal end coupled to the at least one of the first jaw member and the second jaw member.

17. The surgical instrument of claim 14, further comprising a closure actuator having a proximal end and a distal end, the distal end coupled to the spring and the proximal end coupled to a toggle clamp configured to drive the closure actuator, wherein the closure actuator is configured to compress the spring when the closure actuator moves in a distal direction.

18. The surgical instrument of claim 14, further comprising:
   a firing bar having a proximal end and a distal end, wherein the cutting element is coupled to the distal end of the firing bar; and
   a rack coupled to the proximal end of the firing bar, wherein the rack is operatively coupled to the firing plate.

19. The surgical instrument of claim 1, wherein the trigger is configured to actuate for a first stroke and for a second stroke, wherein the first stroke defines a rotation of the trigger from a first position to a second position, wherein the second stroke defines a rotation of the trigger from a third position to a fourth position.

20. The surgical instrument of claim 19, wherein the first stroke causes the spring to apply a first clamping force, wherein the second stroke causes the I-beam member to apply a second clamping force to move the first jaw member relative to the second jaw member.

* * * * *